(12) United States Patent
Chen et al.

(10) Patent No.: US 11,857,572 B2
(45) Date of Patent: Jan. 2, 2024

(54) METHOD FOR PREPARING CAR-T CELL WITH TCM AS MAIN ACTIVE COMPONENT AND USE THEREOF

(71) Applicant: XUANWU HOSPITAL OF CAPITAL MEDICAL UNIVERSITY, Beijing (CN)

(72) Inventors: Zhiguo Chen, Beijing (CN); Yu Zhao, Beijing (CN)

(73) Assignee: XUANWU HOSPITAL OF CAPITAL MEDICAL UNIVERSITY, Beijing (CN)

(*) Notice: Subject to any disclaimer, the term of this patent is extended or adjusted under 35 U.S.C. 154(b) by 529 days.

(21) Appl. No.: 17/061,558

(22) Filed: Oct. 1, 2020

(65) Prior Publication Data
US 2021/0077531 A1 Mar. 18, 2021

Related U.S. Application Data

(63) Continuation of application No. PCT/CN2019/117100, filed on Nov. 11, 2019.

(30) Foreign Application Priority Data

Jun. 13, 2019 (CN) .......................... 201910510234.3

(51) Int. Cl.
| | |
|---|---|
| A61K 35/17 | (2015.01) |
| A61P 35/00 | (2006.01) |
| C07K 16/28 | (2006.01) |
| C12N 5/0783 | (2010.01) |
| C12N 15/86 | (2006.01) |

(52) U.S. Cl.
CPC .............. *A61K 35/17* (2013.01); *A61P 35/00* (2018.01); *C07K 16/2803* (2013.01); *C12N 5/0636* (2013.01); *C12N 15/86* (2013.01); *C07K 2317/622* (2013.01); *C07K 2319/33* (2013.01); *C12N 2501/2302* (2013.01); *C12N 2501/2307* (2013.01); *C12N 2501/2315* (2013.01); *C12N 2510/00* (2013.01); *C12N 2740/15043* (2013.01)

(58) Field of Classification Search
CPC ..... A61K 35/17; A61P 35/00; C07K 16/2803; C07K 2317/622; C07K 2319/33; C12N 5/0636; C12N 15/86; C12N 2501/2302; C12N 2510/00
See application file for complete search history.

(56) References Cited

U.S. PATENT DOCUMENTS

| | | | |
|---|---|---|---|
| 2017/0037369 A1* | 2/2017 | Ramsborg | .............. A61P 35/00 |
| 2019/0119640 A1 | 4/2019 | Ostertag et al. | |

FOREIGN PATENT DOCUMENTS

| | | | |
|---|---|---|---|
| CN | 108101994 A | 6/2016 | |
| CN | 105949325 A | 9/2016 | |
| CN | 108017717 A | 5/2018 | |
| CN | 108135938 | 6/2018 | |
| CN | 108473950 A | 8/2018 | |
| CN | 109069537 A | 12/2018 | |
| CN | 109423478 A | 3/2019 | |
| CN | 109476722 A | 3/2019 | |
| CN | 110358734 A | 10/2019 | |
| EP | 3581200 A1 | 12/2019 | |
| WO | WO-2015095895 A1 * | 6/2015 | ............. A61K 35/17 |
| WO | 2017015427 A1 | 1/2017 | |
| WO | 2018064681 A1 | 4/2018 | |
| WO | 2018218038 A1 | 11/2018 | |

OTHER PUBLICATIONS

Cuzick ("Preventive therapy for cancer", The Lancet Oncology, vol. 18, Issue 8,2017, pp. 472-482) (Year: 2017).*
Le et al. ("Incubation of antigen-sensitized T lymphocytes activated with bryostatin 1 + ionomycin in IL-7 + IL-15 increases yield of cells capable of inducing regression of melanoma metastases compared to culture in IL-2." Cancer Immunol Immunother 58, 1565-1576 (2009) (Year: 2009).*
GenScript, The NWSHPQFEK Tag Antibody, mAb, Mouse, Datasheet, Version: Aug. 17, 2016 (Year: 2016).*
Zhang, Xiaolian, Research Progress of CAR-T Immunotherapy, New Advances in Immunology and Experimental Technology, Chapter 24, 2018, 11 pages.
The Extended European Search Report in European Application No. 19932402.1 dated Aug. 18, 2022, 8 pages.

(Continued)

*Primary Examiner* — Adam Weidner
*Assistant Examiner* — Ashley H. Gao
(74) *Attorney, Agent, or Firm* — METIS IP LLC

(57) ABSTRACT

A method for increasing the proportion of a central memory T cell (Tcm) subset in a CAR-T cell product includes adding an artificial antigenic epitope in a CAR, and activating a CAR-T by the artificial antigenic epitope, wherein the artificial antigenic epitope does not exist in other domains or segments of the CAR. A method for preparing a CAR-T cell includes: introducing the CAR into a T cell; and culturing the CAR-introduced T cell, and performing specific activation in the culture process. The preparation method can not only increase the proportion of CAR-positive T cells in the product, but also can achieve specific in vitro amplification of the Tcm subset in the CAR-positive T cells, and significantly increases the proportion of Tcm in a final product. Clinical trials show that the CAR-T cells have significantly improved amplification capacity in vivo, and improved clinical safety and effectiveness.

1 Claim, 15 Drawing Sheets

Specification includes a Sequence Listing.

(56) References Cited

OTHER PUBLICATIONS

First Office Action of the Chinese application No. 201910510234.3, issued on Mar. 16, 2020.
Second Office Action of the Chinese application No. 201910510234.3, dated Jun. 9, 2020.
State Intellectual Property Office of The P.R.China (ISA/CN), International Search Report for International Application PCT/CN2019/117100, dated Mar. 12, 2020,.
Cartellieri, M. et al., "A Novel Ex Vivo Isolation and Expansion Procedure for Chimeric Antigen Receptor Engrafted Human T Cells.", Plos one,vol. 9, No. (4), Apr. 3, 2014, 1-12.
Liu, Lingfeng et al., "Inclusion of Strep-Tag II in Design of Antigen Receptors for T Cell Immunotherapy", Nat Biotechnol., vol. 34, No. (4), Apr. 30, 2016, 430-434.
Stanley R. Riddell et al., "Adoptive Therapy with Chimeric Antigen Receptor Modified T Cells of Defined Subset Composition", Cancer J., Mar. 1, 2015, 1-10.
Xu, Xuequn et al., CAR-T Design and its Challenges in Ovarian Cancer, Immunological Journal, 2017, 11 pages.
Meng, Shufang et al., Car-T Cell Therapy Product Quality Control Testing Study, Chinese Pharmaceutical Affairs, 2018, 70 pages.
Du, Jun et al., Clinical Application of CAR-T Therapy in Hematology, E-J Transl. Med., 2018, 12 pages.

* cited by examiner

METHOD FOR PREPARING CAR-T CELL WITH TCM AS MAIN ACTIVE COMPONENT AND USE THEREOF

CROSS-REFERENCE TO RELATED APPLICATIONS

This application is continuation of, and claims priority to, International Application No. PCT/CN2019/117100 filed on Nov. 11, 2019, which claims priority to Chinese Patent Application No. CN 201910510234.3 filed on Jun. 13, 2019. The disclosures of these applications are hereby incorporated by reference in their entirety.

SEQUENCE LISTING

The instant application contains a Sequence Listing which has been submitted electronically in ASCII format and is hereby incorporated by reference in its entirety. Said ASCII file, created on Jun. 13, 2019, is named NSequence-2019111106-2.txt and is 30,226 bytes in size.

BACKGROUND

Central memory T cells (Tcm) are a T cell subset with CD45RO+/CD197+ as surface markers. T cells under this subset are differentiated from naive T cells that are stimulated by antigens or non-antigens, and mainly participate in specific memory immune response in vivo. The Tcm subset has a low proportion in the T cell subset obtained from peripheral blood separation. During in vitro culture, Tcm rapidly proliferates in an initial stage of culture, and then the proliferation rate decreases with the increase of culture time.

Adoptive immune cell therapy is a novel anti-tumor therapy means in the current biomedical field. The method mainly includes: extracting a patient's autologous cells, performing activation, modification, culture and amplification in vitro, and then infusing back into the body of the patient, thereby achieving the purpose of treating tumors. CAR-T, a chimeric antigen receptor-modified T cell, is a targeted adoptive immune cell therapy method. This technology modifies a T cell genome by using a genetic modification method so that it can express a CAR receptor capable of recognizing a tumor-specific antigen, thereby breaking through anti-tumor MHC restriction of original T cells, and allowing the T cells to directly kill tumors. For example, CD19-specific CAR-T cells have made breakthrough progresses in treating acute B lymphocytic leukemia and B-cell lymphoma, and have achieved clinical application. However, the current CAR-T treatment technology still has many clinical bottlenecks.

A large number of studies have shown that maintainability of the efficacy of existing CAR-T cells in vivo is not satisfactory. After achieving complete remission in patients receiving treatment, the recurrence rate within one year was as high as 46%. By analyzing and displaying the patient's infused immune cell subset and an infused CAR-T product, the proportion of the Tcm in the product and the proportion of the Tcm in an infused body of a subject are positively correlated with the remission time and the maintainability of CAR-T anti-tumor activity. As the proportion of the Tcm in CAR-positive T cells in the CAR-T product infused into the patient increases, the possibility of the patient receiving long-term remission is greater. Preclinical animal experiments also show that the infusion of CAR-T cells with the Tcm as the main subset can significantly extend the survival time of mice.

A currently known Tcm preparation method is to isolate primary naive T cells from peripheral blood, and they are firstly activated by using CD3 monoclonal antibodies OKT-3 and IL-2. After 24 hours of activation, they are added into a culture medium including IL-7, IL-15, and IL-21 for culture. Cells are harvested after 6-9 days of culture. At this time, the proportion of the Tcm in a final product is about 50%, which is difficult to meet the requirements of clinical infusion.

Due to the proliferation characteristics of the Tcm cell subset, during in vitro culture, the proportion of the Tcm cell subset may decreases rapidly as the culture time extends. Therefore, the short-term culture process cannot ensure that a sufficient number of target cells are obtain, and increasing the culture number of initial seed cells can cause a sharp increase in preparation costs. At present, the preparation process of the CAR-T cannot guarantee that under the premise that the subject has a sufficient number of cells to be infused, high-purity Tcm cells are in the infused product. Therefore, how to use a cost-effective method to obtain a cell product with the Tcm as the main active component is a technical problem in the industry.

SUMMARY

The present disclosure relates to the technical field of gene therapy and cell therapy, in particular to a method for preparing a CAR-T cell with Tcm as a main active component and use thereof.

Various embodiments of the present disclosure provide a method for preparing a CAR-T cell with Tcm as a main active component and use thereof.

For this purpose, the present disclosure provides a method for increasing the proportion of a central memory T cell (Tcm) subset in a CAR-T cell product. The method includes adding an artificial antigenic epitope in a CAR, and activating a CAR-T by the artificial antigenic epitope, wherein the artificial antigenic epitope does not exist in other domains or segments of the CAR.

Further, the artificial antigenic epitope has no or substantially no negative effects on functions of the other domains or segments of the CAR; and the artificial antigenic epitope can activate the CAR-T when it is bound.

Further, the artificial antigenic epitope is located in an extracellular domain of the CAR, between the extracellular domain and a hinge region, or between the hinge region and a transmembrane structure.

Further, the length of the artificial antigenic epitope is 7-15aa, preferably 8-12aa.

Further, an amino acid sequence of the artificial antigenic epitope is SEQ ID NO: 1, SEQ ID NO: 2, or SEQ ID NO: 3.

Further, the CAR-T is activated by using a molecule that specifically recognizes the artificial antigenic epitope in combination with the artificial antigenic epitope, and the molecule that specifically recognizes the artificial antigenic epitope is preferably an antibody molecule.

Further, the step of activating the CAR-T by the artificial antigenic epitope is after the step of introducing the CAR into T cells.

Further, the step of activating the CAR-T by the artificial antigenic epitope includes culturing the CAR-T in a culture medium containing IL-7, IL-2, and The concentrations of the IL-7, the IL-2, and the IL-15 are 10-200 ng/mL, 20-1000 IU/mL, and 1-50 ng/mL, respectively.

The method in the present disclosure is an in vitro method. Although the CAR-T prepared by the method has a good tumor treatment effect, a direct purpose of the method of the present disclosure is to improve the proportion of the central memory T cell (Tem) subset in the in vitro CAR-T cell, and the method itself does not involve any in vivo operation steps.

Specifically, according to a first aspect, the present disclosure provides a method for preparing the CAR-T cell, including:

(1) introducing the chimeric antigen receptor (CAR) into a T cell; and
(2) culturing the CAR-introduced T cell, and performing specific activation in the culture process.

The CAR has the artificial antigenic epitope.

The specific activation includes adding an anti-artificial antigenic epitope antibody in the culture process, and the anti-artificial antigenic epitope antibody can specifically recognize the artificial antigenic epitope.

The protein structure of the CAR sequentially includes the following domains: an extracellular domain, an optional hinge region, a transmembrane domain, and an intracellular domain. The extracellular domain includes an optional signal peptide and an antigen-binding domain, the antigen-binding domain includes an antibody or an antibody fragment having antigen-binding activity, and the antibody or the antibody fragment at least includes a heavy chain variable region and a light chain variable region.

Further, the artificial antigenic epitope is located in the extracellular domain of the CAR, between the extracellular domain and the hinge region, or between the hinge region and the transmembrane domain. In a specific implementation, the artificial antigenic epitope is located in the extracellular domain of the CAR. In a preferred embodiment, the artificial antigenic epitope is located between the signal peptide and the antigen-binding domain. In another preferred embodiment, the artificial antigenic epitope is located in the antigen-binding domain. Further, the artificial antigenic epitope is located between the heavy chain variable region and the light chain variable region.

Further, the artificial antigenic epitope is one of the following (a1)-(a3):

(a1) E-tag, with an amino acid sequence of KPLPEVTDEY (SEQ ID NO: 1);
(a2) Strep-tag, with an amino acid sequence of WSHPQFEK (SEQ ID NO: 2); and
(a3) Strep-tag II, with an amino acid sequence of NWSHPQFEK (SEQ ID NO: 3).

When the artificial antigenic epitope is the E-tag, the anti-artificial antigenic epitope antibody is an anti-E-tag antibody, and the anti-E-tag antibody can specifically recognize the E-tag. In a specific implementation, an amino acid sequence of the anti-E-tag antibody is SEQ ID NO: 4.

When the artificial antigenic epitope is the Strep-tag, the anti-artificial antigenic epitope antibody is an anti-Strep-tag antibody, and the anti-Strep-tag antibody can specifically recognize the Strep-tag. In a specific implementation, the anti-Strep-tag antibody is purchased from Bio-Rad (Art.No.: MCA2488).

When the artificial antigenic epitope is the Strep-tag II, the anti-artificial antigenic epitope antibody is an anti-Strep-tag II antibody, and the anti-Strep-tag II antibody can specifically recognize the Strep-tag II. In a specific implementation, the anti-Strep-tag II antibody is purchased from Genscript (Art.No.: A01732).

Further, the method for preparing the T cell in step (1) includes: isolating the T cell from peripheral blood, and performing T-cell activation on the isolated T cell.

Further, the T-cell activation in step (1) includes culturing the isolated T cell in a first culture medium, and the first culture medium includes OKT-3 and IL-2. Further, in the first culture medium, the concentration of OKT-3 is 5-200 ng/mL, 10-100 ng/mL, more preferably 50-80 ng/mL, for example, 50 ng/mL, 60 ng/mL, 70 ng/mL, or 80 ng/mL; and the concentration of IL-2 is 20-1000 IU/mL, preferably 50-500 IU/mL, more preferably 200-500 IU/mL, for example, 200 IU/mL, 300 IU/mL, 400 IU/mL, or 500 IU/mL.

The first culture medium can be prepared by using a culture medium commonly used in the art. In a specific implementation, the first culture medium can be prepared by the following culture medium, including but not limited to: an X-VIVO15 culture medium (Lonza), a KBM581 serum-free culture medium (Corning), an RPMI1640 culture medium containing 10% of FBS (Gbico), or an RPMI1640 culture medium containing 10% of human AB serum (Gbico).

Further, the culture time for the T-cell activation is 4-72 h, preferably 24-36 h, for example, 24 h, 28 h, 32 h, or 36 h, and in a preferred embodiment, it is 24 h.

Further, the culture medium used for culture in step (2) is a second culture medium, and the second culture medium includes IL-7, IL-2, and IL-15. Further, in the second culture medium, the concentration of IL-7 is 10-200 ng/mL, preferably 20-100 ng/mL, more preferably 80-100 ng/mL, for example, 80 ng/mL, 90 ng/mL, or 100 ng/mL; the concentration of IL-2 is 20-1000 IU/mL, preferably 50-500 IU/mL, more preferably 200-500 IU/mL, for example, 200 IU/mL, 300 IU/mL, 400 IU/mL, or 500 IU/mL; and the concentration of IL-15 is 1-50 ng/mL, preferably 5-30 ng/mL, more preferably 10-20 ng/mL, for example, 10 ng/mL, 12 ng/mL, 14 ng/mL, 16 ng/mL, 18 ng/mL, or 20 ng/mL.

The second culture medium can be prepared by using a culture medium commonly used in the art. In a specific implementation, the second culture medium can be prepared by the following culture medium, including but not limited to: an X-VIVO15 culture medium (Lonza), a KBM581 serum-free culture medium (Corning), an RPMI1640 culture medium containing 10% of FBS (Gbico), or an RPMI1640 culture medium containing 10% of human AB serum (Gbico).

Further, the culture time in step (2) is 9-14 days, preferably 9-12 days, for example, 9 days, 10 days, 11 days, or 12 days; and in a preferred embodiment, it is 12 days.

Further, the specific activation in step (2) includes: adding the anti-artificial antigenic epitope antibody into the second culture medium from the $m^{th}$ day of the culture process to the end of the culture, where m is an integer selected from 6-9, for example, 6, 7, 8, or 9, and in a preferred embodiment, m=6.

Further, in step (2), the concentration of the anti-artificial antigenic epitope antibody is 1-50 μg/mL, preferably 5-30 μg/mL, more preferably 10-25 μg/mL, for example, 10 μg/mL, 15 μg/mL, 20 μg/mL, or 25 μg/mL; and in a preferred embodiment, it is 20 μg/mL.

Further, in step (2), the method for adding the anti-artificial antigenic epitope antibody is selected from the following groups: directly adding the anti-artificial antigenic epitope antibody into the culture medium, or encapsulating the anti-artificial antigenic epitope antibody in a culture container, or a combination thereof.

Further, the method of introducing the CAR into the T cell in step (1) is to introduce into the T cell by means of viral infection or to introduce into the T cell by means of non-viral infection. The virus in the viral infection method is selected from the following viruses: adenovirus, retrovirus, lentivirus, herpes virus, and adeno-associated virus; and the non-viral infection method is a liposome method, a microinjection method, a calcium phosphate co-precipitation method, an electrophoretic transfer method, or a DEAE-dextran transfection method.

Further, the step (1) is introducing the CAR into the T cell by virus infection. In a preferred embodiment, the step (1) specifically includes the following steps:

S1: constructing a CAR virus expression vector;

S2: introducing the CAR virus expression vector prepared in step S1 into a corresponding packaging cell for virus packaging to obtain a CAR-encoded virus;

S3: isolating the T cell from peripheral blood, and performing T-cell activation on the isolated T cell; and S4: using the CAR-encoded virus prepared in step S2 to infect the T cell prepared in step S3.

Further, the virus expression vector is an adenovirus expression vector, a retrovirus expression vector, a lentivirus expression vector, a herpes virus expression vector, or an adeno-associated virus expression vector. In a preferred embodiment, the virus expression vector is the lentivirus expression vector.

According to a second aspect, the present disclosure provides CAR-T cells having a high proportion of central memory T cell (Tcm) subset, wherein the CAR-T cell is prepared by the method of the present disclosure.

According to a third aspect, the present disclosure provides use of the CAR-T cells in preparation of a medicament or a preparation for preventing and/or treating cancers or tumors.

At the same time, the present disclosure further provides use of the CAR-T cells in preventing and/or treating cancers or tumors.

Further, the tumors are selected from the following group consisting of a hematological tumor, a solid tumor, or a combination thereof.

Further, the hematological tumor is selected from the following group consisting of acute myelocytic leukemia (AML), multiple myeloma (MM), chronic lymphocytic leukemia (CLL), acute lymphoblastic leukemia (ALL), and diffuse large B-cell lymphoma (DLBCL), non-Hodgkin's lymphoma (NHL), or combinations thereof.

Further, the solid tumor is selected from the following group consisting of gastric cancer, gastric cancer peritoneal metastasis, liver cancer, leukemia, kidney tumor, lung cancer, small intestine cancer, bone cancer, prostate cancer, colorectal cancer, breast cancer, colorectal cancer, cervical cancer, ovarian cancer, lymph cancer, nasopharyngeal carcinoma, an adrenal tumor, a bladder tumor, non-small cell lung cancer (NSCLC), brain glioma, endometrial cancer, mesothelioma, pancreatic cancer, multiple myeloma, or combinations thereof.

In a previous research, the inventor of the present disclosure reported a CAR molecule with the artificial antigenic epitope. A CAR-positive target cell can be efficiently sorted by a secondary sorting method to improve the proportion of positive CAR-T cells in a final product (CN108017717A). Based on this research, the inventor unexpectedly discovered that in the preparation process, the specific activation of the CAR-introduced T cell on the anti-artificial antigenic epitope antibody can not only increase the proportion of CAR-positive T cells in the final product, but also can significantly increase the proportion of the Tcm in the CAR-positive T cells, thereby bringing unexpected technical effects.

The present disclosure has the following advantages as compared with the prior art:

1. the preparation method provided in the present disclosure can increase the proportion of the CAR-positive T cells in the product without specifically sorting the CAR-introduced T cells;
2. the preparation method provided in the present disclosure can achieve specific in vitro amplification of the Tcm subset in the CAR-positive T cells, and can significantly increase the proportion of the Tcm in the final product;
3. the preparation method provided in the present disclosure overcomes the technical problem that the Tcm cannot be long-term cultured in vitro, realizes long-term in vitro culture of the Tem, and effectively improves the yield of the Tcm; and in the prior art, the proportion of the Tem began to decrease when cultured to the $6^{th}$ day, while in the technical solution of the present disclosure, when cultured to the $12^{th}$ day, the proportion of the Tcm can still be maintained at a high level;
4. compared with the prior art, the CAR-T cells prepared in the present disclosure have good killing-related cytokine release activity both in in vitro and in vivo environments, and has better and longer-lasting anti-tumor activity; and
5. clinical trials show that the CAR-T cells prepared in the present disclosure have significantly better amplification capacity in vivo than the prior art, and has better clinical safety and effectiveness.

BRIEF DESCRIPTION OF THE DRAWINGS

Various other advantages and benefits become apparent to those of ordinary skilled in the art upon reading the detailed description of preferred implementations below. The drawings are only for the purpose of illustrating preferred implementations and are not to be considered as a limitation to the present disclosure. In the drawings.

DETAILED DESCRIPTION

Figure 1:
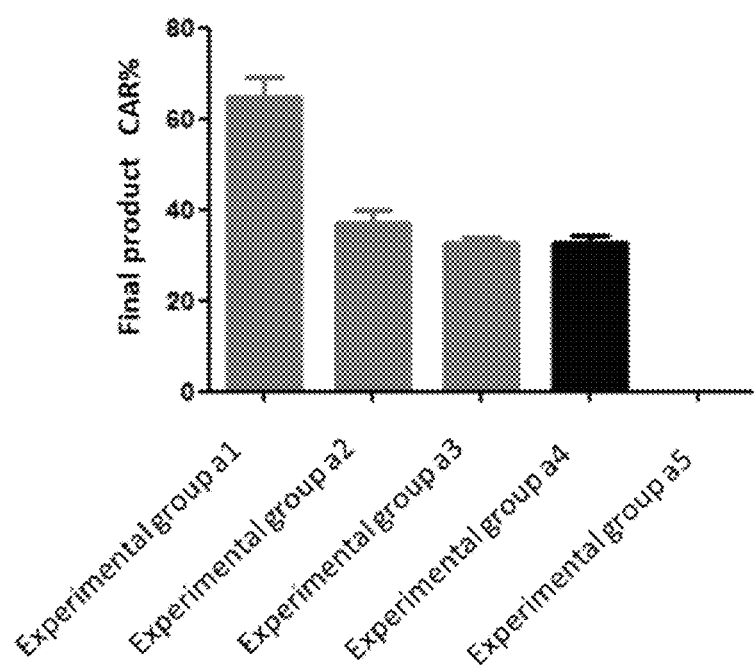
FIG. 1 illustrates proportions of CAR-positive T cells in a cell product prepared in each experimental group in embodiment 3.
Figure 2:
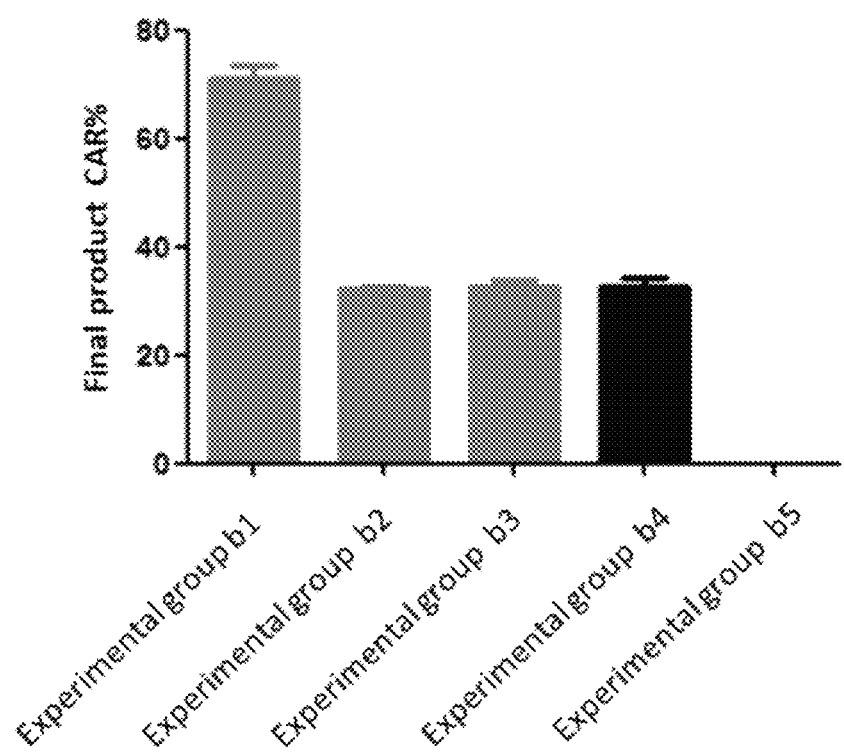
FIG. 2 illustrates proportions of CAR-positive T cells in a cell product prepared in each experimental group in embodiment 4.
Figure 3:
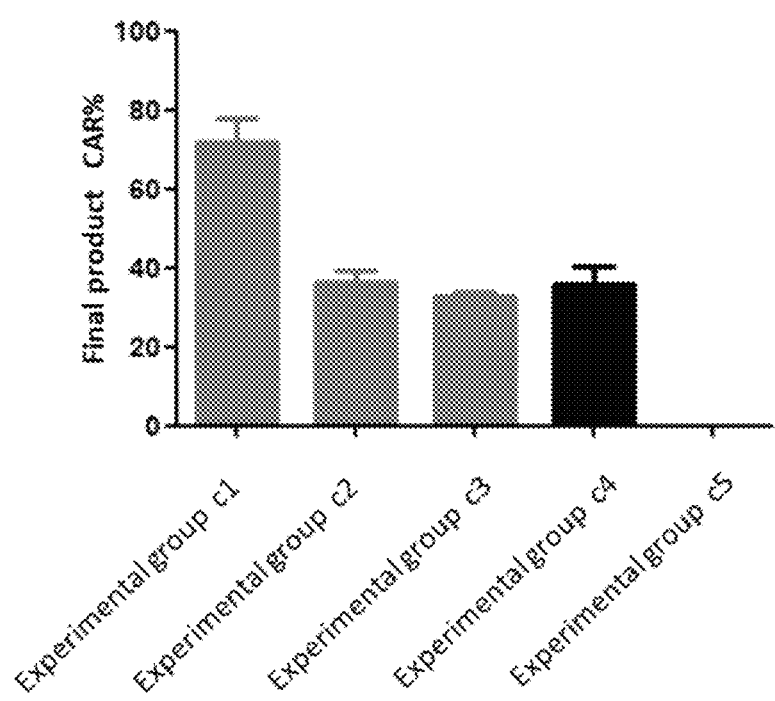
FIG. 3 illustrates proportions of CAR-positive T cells in a cell product prepared in each experimental group in embodiment 5.
Figure 4:
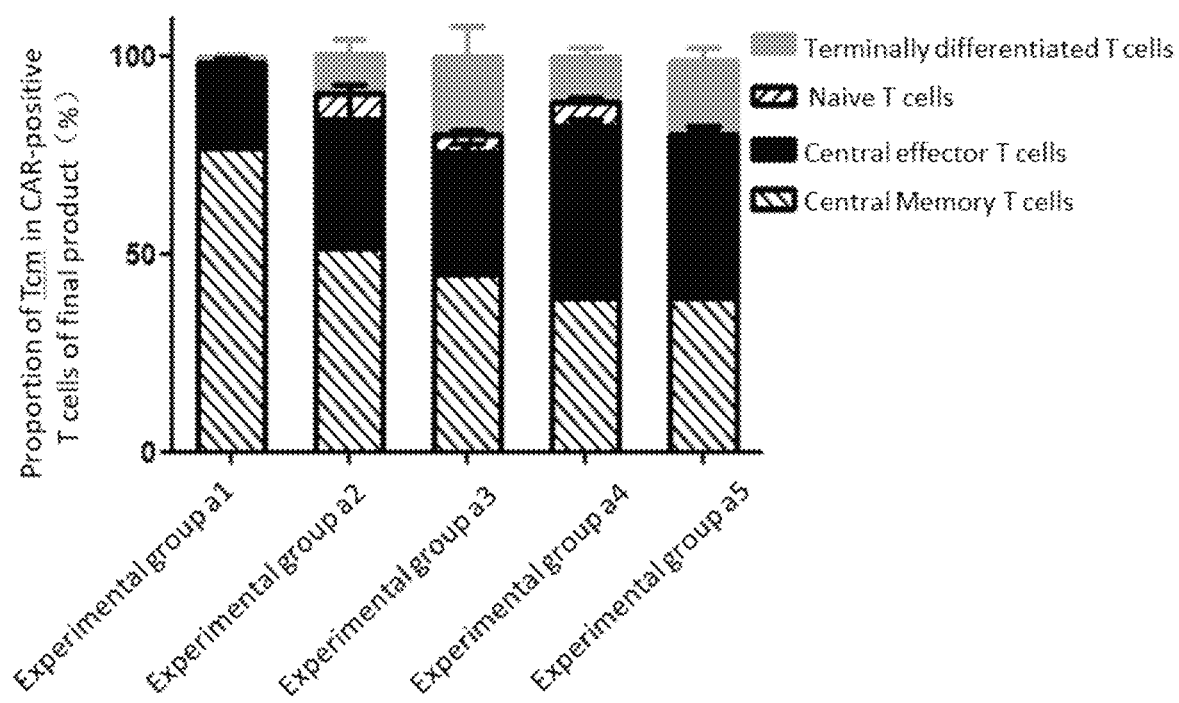
FIG. 4 illustrates proportions of Tem in CAR-positive T cells in a cell product prepared in each experimental group in embodiment 3.
Figure 5:
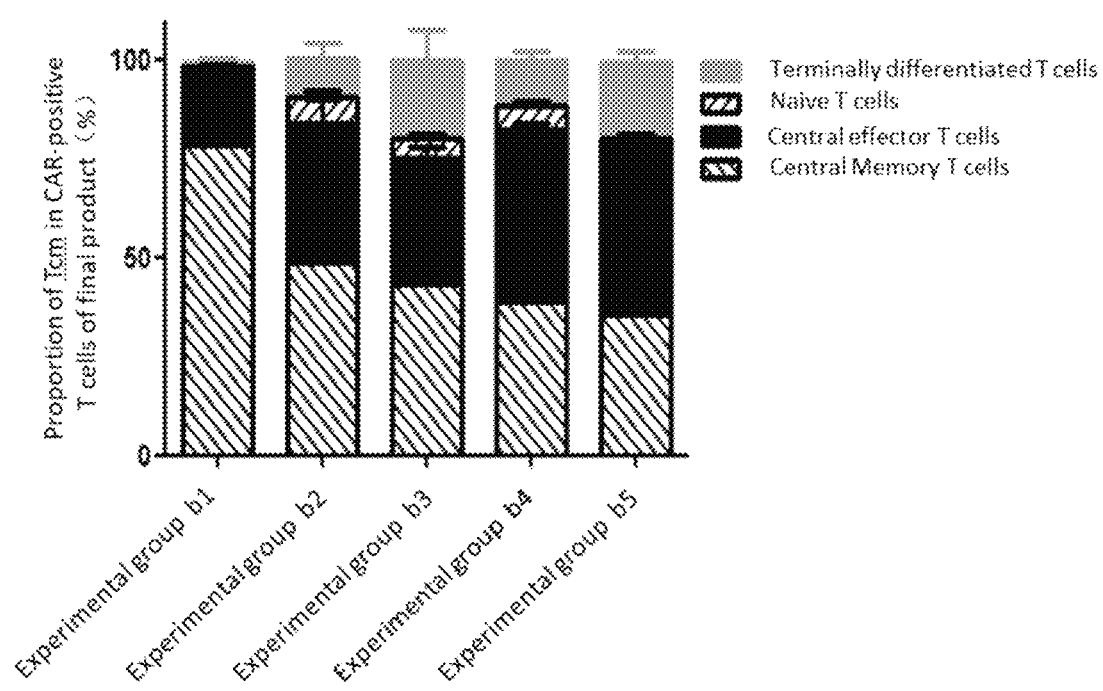
FIG. 5 illustrates proportions of Tcm in CAR-positive T cells in a cell product prepared in each experimental group in embodiment 4.
Figure 6:
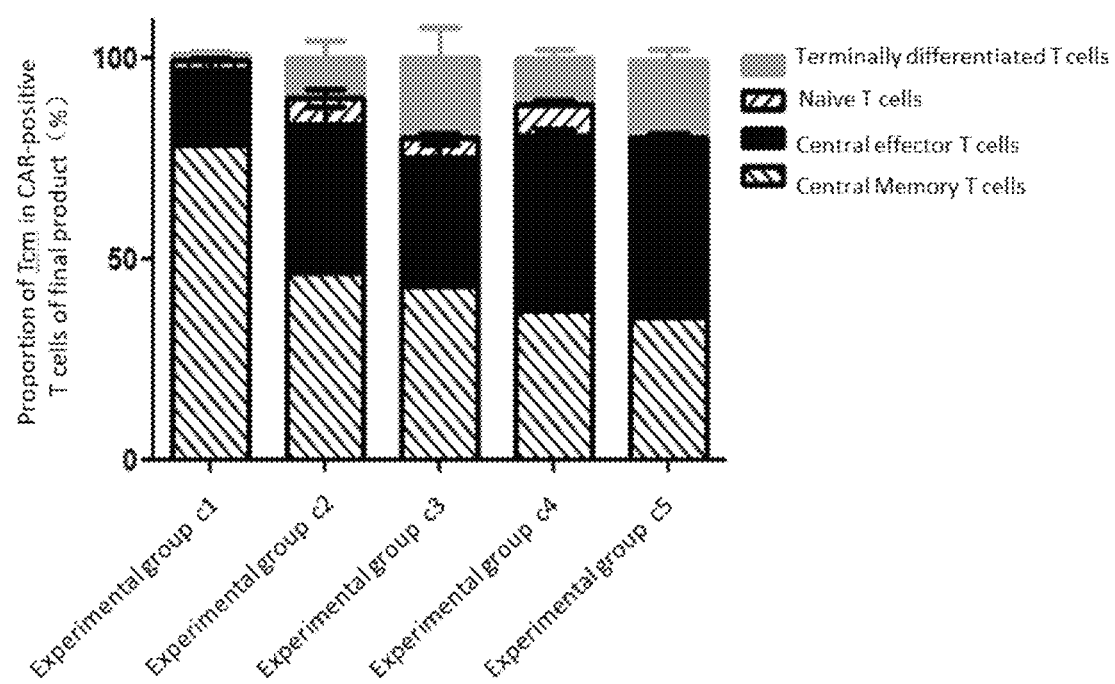
FIG. 6 illustrates proportions of Tcm in CAR-positive T cells in a cell product prepared in each experimental group in embodiment 5.

The following will describe exemplary embodiments of the present disclosure in more detail with reference to the drawings. Although the exemplary embodiments of the present disclosure are shown in the drawings, it should be understood that the present disclosure can be implemented in various forms and should not be limited by the embodiments set forth herein. On the contrary, these embodiments are provided to more thoroughly understand the present disclosure, and to fully convey the scope of the present disclosure to those skilled in the art.

In order to understand the present disclosure more easily, certain terms are first defined. As used in this disclosure, each term below has its meaning given below unless otherwise specified herein.

The protein structure of a chimeric antigen receptor (CAR) sequentially includes an extracellular domain, an optional hinge region, a transmembrane domain, and an intracellular domain. The extracellular domain includes an optional signal peptide and an antigen-binding domain, and the antigen-binding domain can directly recognize a tumor associated antigen (tumor associated antigen, TAA) without the need to recognize the antigen in a form of MHC/antigen peptide complex.

The antigen-binding domain described herein includes an antibody or a fragment thereof having antigen-binding activity, and the antibody or the antibody fragment at least includes a heavy chain variable region and a light chain variable region. Specifically, the antigen-binding domain includes a Fab fragment having antigen-binding activity, a Fab' fragment, an F (ab')2 fragment, or a single Fv fragment. An Fv antibody includes a heavy chain variable region and a light chain variable region of the antibody, but has no constant region, and has a smallest antibody fragment with all antigen-binding sites. Generally, the Fv antibody also includes a polypeptide joint between the heavy chain variable region and the light chain variable region and is capable of forming a structure required for antigen binding. The antigen-binding domain is usually an scFv (single-chain variable fragment).

In the method for preparing a chimeric antigen receptor-modified T cell provided in the present disclosure, the CAR has an artificial antigenic epitope, and the artificial antigenic epitope has the following characteristics:

(a) the artificial antigenic epitope is absent from other domains or segments of the CAR;

(b) when the artificial antigenic epitope is in a free state or present in the CAR, the artificial antigenic epitope can be recognized by the anti-artificial antigenic epitope antibody; and (c) the binding between the CAR and the antigen targeted by the CAR is not affected or substantially not affected.

The artificial antigenic epitope can be located in the extracellular domain of the CAR, specifically, the artificial antigenic epitope may be located in the extracellular domain of the CAR or between the extracellular domain and the hinge region, or between the hinge region and the transmembrane domain. In a specific implementation, the artificial antigenic epitope is located in the extracellular domain of the CAR. In a preferred embodiment, the artificial antigenic epitope is located between the signal peptide and the antigen-binding domain. In another preferred embodiment, the artificial antigenic epitope is located in the antigen-binding domain. Further, the artificial antigenic epitope is located between the heavy chain variable region and the light chain variable region.

In the present disclosure, "specific recognition", that is, "specific binding", indicates that an anti-artificial antigenic epitope antibody can specifically recognize the artificial antigenic epitope. When the artificial antigenic epitope is in the free state or present in the CAR, the anti-artificial antigenic epitope antibody can specifically recognize the artificial antigenic epitope, and the anti-artificial antigenic epitope antibody does not recognize or bind to other molecules in the culture system or domains other than the artificial antigenic epitope in the CAR.

The anti-artificial antigenic epitope antibody in the present disclosure may be selected from a commercial antibody, or may be prepared and obtained with the artificial antigenic epitope as an antigen and by a conventional technique of antibody preparation.

If a specific technology or condition is not indicated in the embodiments, the embodiments should be performed according to the technology or condition described in literatures (For example, refer to "Molecular Cloning: A Laboratory Manual" written by J. Sambrook et al. and translated by He Fuchu et al., Fourth Edition, Science Press; and "Short Protocol In Immunology" written by J. E. Coligan et al. and translated by Cao XueTao et al., Science Press) in the art or according to product descriptions.

Fetal bovine serum FBS, DMEM culture medium, D-PBS culture medium, and RPMI1640 culture medium were purchased from Gbico; OKT-3 was purchased from Pepro Tech; IL-2, IL-7, and IL-15 were purchased from Thermo Fisher; X-VIVO15 was purchased from LONZA; SmAb (amino acid sequence is SEQ ID NO: 4) was prepared and provided by Sino Biological Inc.; MCA2488 was purchased from Bio-Rad; A01732 was purchased from Genscript; Human kidney cell line HEK293T and human lymphoma cell line Raji were purchased from American type culture collection (ATCC); NOD/SCID IL2Rγc-/-immunodeficient mice were purchased from Beijing Vitalstar Biotechnology Co., Ltd.; and Raji-Luci cell line was purchased from Beijing Vitalstar Biotechnology Co., Ltd.

Embodiment 1 Construction of Expression Vector of Chimeric Antigen Receptor (CD19sCAR-1)

In this embodiment, an anti-human CD19 humanized single chain antibody is used as an example to construct a CD19-targeted chimeric antigen molecule CD19sCAR-1 (for amino acid sequence, see SEQ ID NO: 5). The CAR molecule can target a CD19 antigen and contains an artificial antigenic epitope E-tag (for amino acid sequence, see SEQ ID NO: 1).

Full sequence synthesis is performed on an open reading frame sequence (for the nucleotide sequence, see SEQ ID NO: 6) of CD19sCAR-1 by using a chemical synthesis method, restriction sites were added at both ends of the sequence, and the sequence obtained from synthesis was inserted into the downstream of a CMV promoter of a lentiviral expression vector pLenti6.4 containing the CMV promoter by a gene cloning method. A lentiviral expression vector of the CD19sCAR-1 is obtained. The vector is transformed into an Stbl3 competent engineering strain for storage and subsequent preparation.

At the same time, CD19CAR was constructed as a control CAR molecule. The CD19CAR can target the CD19 antigen, is different from the CD19sCAR-1 in that the CD19CAR does not contain an artificial antigenic epitope and its amino acid sequence is shown in SEQ ID NO: 7.

The full sequence synthesis is performed on an open reading frame sequence (for the nucleotide sequence, see SEQ ID NO: 8) of the CD19CAR by using the chemical synthesis method, restriction sites were added at both ends of the sequence, and the sequence obtained from synthesis was inserted into the downstream of a CMV promoter of the lentiviral expression vector pLenti6.4 containing the CMV promoter by the gene cloning method. A lentiviral expression vector of the CD19CAR is obtained. The vector is transformed into the Stbl3 competent engineering strain for storage and subsequent preparation.

Embodiment 2 Preparation of Chimeric Antigen Receptor (CD19sCAR-1)-Encoded Virus In this embodiment, lentiviruses respectively encoding a CD19sCAR-1, a CD19CAR, and EGFP were prepared. Specific steps are as follows:

HEK293T was used as a packaging cell to prepare a chimeric antigen receptor-encoded virus. HEK293T cells in a logarithmic growth phase are dissociated, centrifuged at 800 rpm for 5 min, and resuspended in a DMEM culture medium containing 10% FBS after a culture medium was discarded. After the cells were counted, the density of a cell suspension was adjusted to $3.6 \times 10^6$/ml, and placed in a cell incubator at 37° C. for use.

The transfection of the virus packaging plasmid was performed by using a Lipofectamine 3000 kit (from Thermo Fisher) and following kit instructions. Three kinds of plasmids required for lentivirus packaging, including a lentiviral expression vector (respectively using a CD19sCAR-1 lentiviral expression vector, a CD19CAR lentiviral expression vector, and a lentiviral vector pLenti6.4-CMV-EGFP that were prepared in Embodiment 1), plasmid psPAX2 encoding viral nucleocapsid protein Gag/Pol and Rev, and plasmid pVSVG encoding a viral envelope protein were mixed with Lipofectamine 3000 to formulate a DNA liposome complex in accordance with a recommended ratio in instructions, standing for 15 min at room temperature. After standing was ended, a 6-well culture plate was taken, the DNA liposome complex is added to the 6-well plate, with 1 ml per well, and the HEK293T cell suspension prepared previously was gently mixed to be added to the 6-well plate, and evenly mixed with the liposome complex. The culture plate was placed in the incubator to continue the culture, and a culture supernatant containing the virus was respectively collected at the $24^{th}$ h and the $48^{th}$ h of culture. After the supernatant was collected for the last time, the supernatant 2000 g was centrifuged for 10 min, and filtered through a 0.45 μm filter membrane to prepare the lentiviruses respectively encoding the CD19sCAR-1, the CD19CAR, and the EGFP, and after packaging, the lentiviruses were stored and frozen at −80° C. for stand-by use.

Embodiment 3 Preparation of Chimeric Antigen Receptor (CD19sCAR-1)-Modified T Cell Peripheral blood mononuclear cells (PBMCs) were isolated by an Ficol-Hypaque density gradient centrifugation method. The PMBCs were resuspended by D-PBS to adjust the density to $0.5 \times 10^6$/mL. Sorted magnetic beads were added according to the 1:1 ratio of the absolute number of T cells and the CD3/CD28 sorted magnetic beads, and were mixed gently and evenly at room temperature for 20 min. CD3+ T cells sorting is performed on an evenly mixed cell-magnetic bead suspension by using a sorting magnetic stand. T cell activation is performed on the sorted T cells: resuspending the T cells at $1 \times 10^6$/mL by using an X-VIVO15 culture medium containing 50 ng/mL OKT-3 and 500 IU/mL IL-2, inoculating into the incubator for the culture, with culture conditions of 37° C. and 5% $CO_2$ saturated humidity incubator for culture for 24 h. After the T cells were activated, the cells were collected in a 50 mL centrifuge tube and counted to adjust the cell density to $3 \times 10^6$/mL.

The harvested cells were grouped according to a grouping method in Table 1 for performing in vitro culture. SmAb represents a monoclonal antibody that targets the artificial antigenic epitope E-tag, and the negative control group is a treatment group that infects the T cells with a lentivirus encoding EGFP.

TABLE 1

Experimental group grouping (a)

| Serial number | Grouping NO. | Treatment and culture method |
| --- | --- | --- |
| 1 | Experimental group a1 | Specific activation with SmAb after CD19sCAR-1 infection |
| 2 | Experimental group a2 | No specific activation with SmAb after CD19sCAR-1 infection |
| 3 | Experimental group a3 | Specific activation with SmAb after CD19CAR infection |
| 4 | Experimental group a4 | No specific activation with SmAb after CD19CAR infection |
| 5 | Experimental group a5 | Negative control group |

The activated T cells were grouped according to the grouping method in Table 1, and then respectively infected with the lentiviruses encoding the CD19sCAR-1, the CD19CAR, and the EGFP prepared in Embodiment 2. After infection for 24 h, the cells of each treatment group were transferred to the X-VIVO15 culture medium containing 80 ng/mL IL-7, 500 IU/mL IL-2, and 20 ng/mL IL-15 for culture, with culture conditions of 37° C. and the 5% $CO_2$ saturated humidity incubator. On the $6^{th}$ day of culture, according to the treatment method of experimental grouping, the experimental group 1 and the experimental group 3 were specifically activated. The processing method was: transferring cells from the experimental group 1 and the experimental group 3 to the incubator coated with 20 μg/mL SmAb antibodies, and continuously culturing with an X-VIVO15 culture medium containing 80 ng/mL IL-7, 500 IU/mL m-2, and 20 ng/mL IL-15 under the same conditions.

During the culture, fluid infusion was performed on the cells every 2-3 days according to the growth of the cells. After that, the cells of each group were continuously cultured until the $12^t h$ day, and cell products were harvested separately.

Embodiment 4 Preparation of Chimeric Antigen Receptor (CD19sCAR-2)-Modified T Cell In this embodiment, a CD19-targeted chimeric antigen molecule CD19sCAR-2 (for amino acid sequence, see SEQ ID NO: 9, and for the nucleotide sequence of an open reading frame, see SEQ ID NO: 10) was constructed. A CAR molecule can target a CD19 antigen and contains an artificial antigenic epitope Strep-tag (for amino acid sequence, see SEQ ID NO: 2). Specific steps of the preparation of the chimeric antigen receptor (CD19sCAR-2)-modified T cell are as follows:

(1) Constructing the Expression Vector of the CD19sCAR-2

The experimental step is the same as that of Embodiment 1, except that the Embodiment 1 uses the sequence of CD19sCAR-1, and this step uses the sequence of the CD19sCAR-2;

(2) Preparing a CD19sCAR-2 Encoded Virus

The experimental step is the same as that of Embodiment 2, except that Embodiment 2 uses a CD19sCAR-1 lentiviral expression vector prepared in Embodiment 1, and this step uses a CD19sCAR-2 lentiviral expression vector prepared in step (1); and (3) Preparing a CDsCAR-2-Modified T Cell The experimental step is the same as that of Embodiment 3, except that the grouping in Embodiment 3 uses Table 1, and the grouping in this step uses Table 2, and preparation is conducted according to Table 2. Cell products of each group were prepared separately.

TABLE 2

Experimental group grouping (b)

| Serial number | Grouping NO. | Treatment and culture method |
|---|---|---|
| 1 | Experimental group b1 | Specific activation with MCA2488 after CD19sCAR-2 infection |
| 2 | Experimental group b2 | No specific activation with MCA2488 after CD19sCAR-2 infection |
| 3 | Experimental group b3 | Specific activation with MCA2488 after CD19CAR infection |
| 4 | Experimental group b4 | Same as experimental group a4 |
| 5 | Experimental group b5 | Same as experimental group a5 |

Embodiment 5 Preparation of Chimeric Antigen Receptor (CD19sCAR-3)-Modified T Cell In this embodiment, a CD19-targeted chimeric antigen molecule CD19sCAR-3 (for amino acid sequence, see SEQ ID NO: 11, and for the nucleotide sequence of an open reading frame, see SEQ ID NO: 12) was constructed. A CAR molecule can target a CD19 antigen and contains an artificial antigenic epitope Strep-tag II (for amino acid sequence, see SEQ ID NO: 3). Specific steps of the preparation of the chimeric antigen receptor (CD19sCAR-3)-modified T cell are as follows:

Constructing the Expression Vector of CD19sCAR-3

The experimental step is the same as that of Embodiment 1, except that Embodiment 1 uses the sequence of CD19sCAR-1, and this step uses the sequence of CD19sCAR-3;

Preparing a CD19sCAR-3 Encoded Virus

The experimental step is the same as that of Embodiment 2, except that Embodiment 2 uses a CD19sCAR-1 lentiviral expression vector prepared in Embodiment 1, and this step uses a CD19sCAR-3 lentiviral expression vector prepared in step (1); and Preparing a CDsCAR-3-Modified T Cell The experimental step is the same as that of Embodiment 3, except that the grouping in Embodiment 3 uses Table 1, and the grouping in this step uses Table 3, and preparation is conducted according to Table 3. Cell products of each group were prepared separately.

TABLE 3

Experimental group grouping (c)

| Serial number | Grouping NO. | Treatment and culture method |
|---|---|---|
| 1 | Experimental group c1 | Specific activation with A01732 after CD19sCAR-3 infection |
| 2 | Experimental group c2 | No specific activation with A01732 after CD19sCAR-3 infection |
| 3 | Experimental group c3 | Specific activation with A01732 after CD19CAR infection |
| 4 | Experimental group c4 | Same as experimental group a4 |
| 5 | Experimental group c5 | Same as experimental group a5 |

Embodiment 6 Proportion of CAR-Positive T Cells and Tcm in a Cell Product

Three independent batches of experiments were counted, the final products of each experimental group prepared in Embodiments 3-5 were respectively subjected to flow detection analysis, and results of the flow detection analysis are shown in FIG. 1-6. It can be learned from FIG. 1-3 that the proportion of CAR-positive T cells in the final products of the experimental group a1, b1, and c1 is significantly higher than that of other experimental groups, indicating that the preparation method provided in the present disclosure can promote the proliferation of the CAR-positive T cells and improve its proportion in the final products. It can be learned from FIG. 4-6 that the proportion of Tcm in the CAR-positive T cells in the experimental group a1, b1, and c1 is about 80%, significantly higher than that of other experimental groups.

Figure 7:
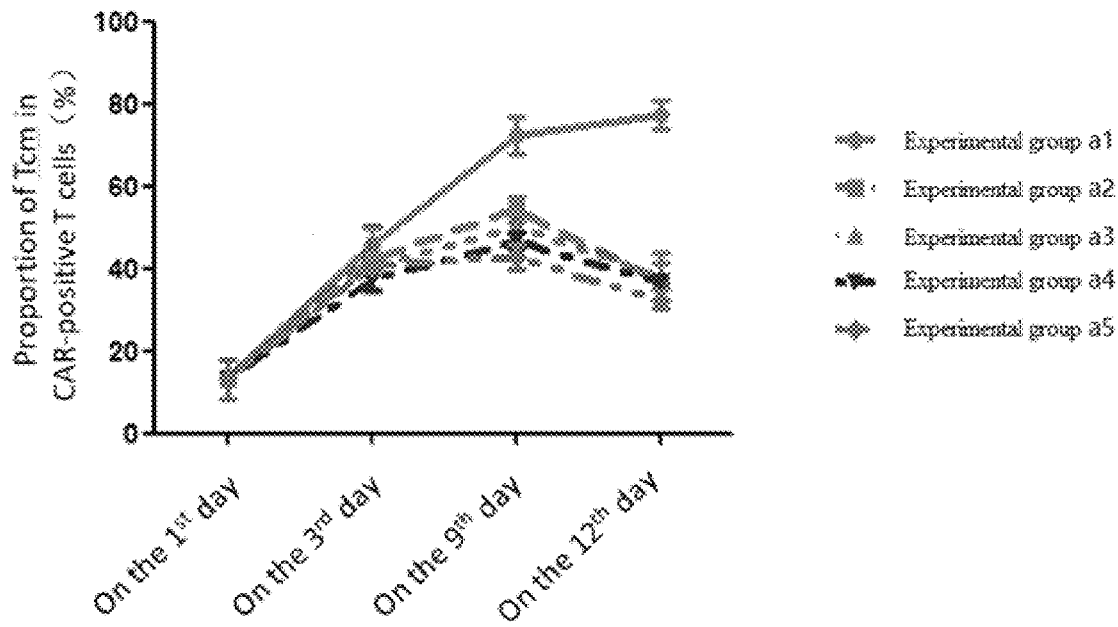
FIG. 7 illustrates changes of the proportion of the Tcm in a culture system with the increase of the culture time during the preparation of a cell product in each experimental group in embodiment 3.
Figure 8:
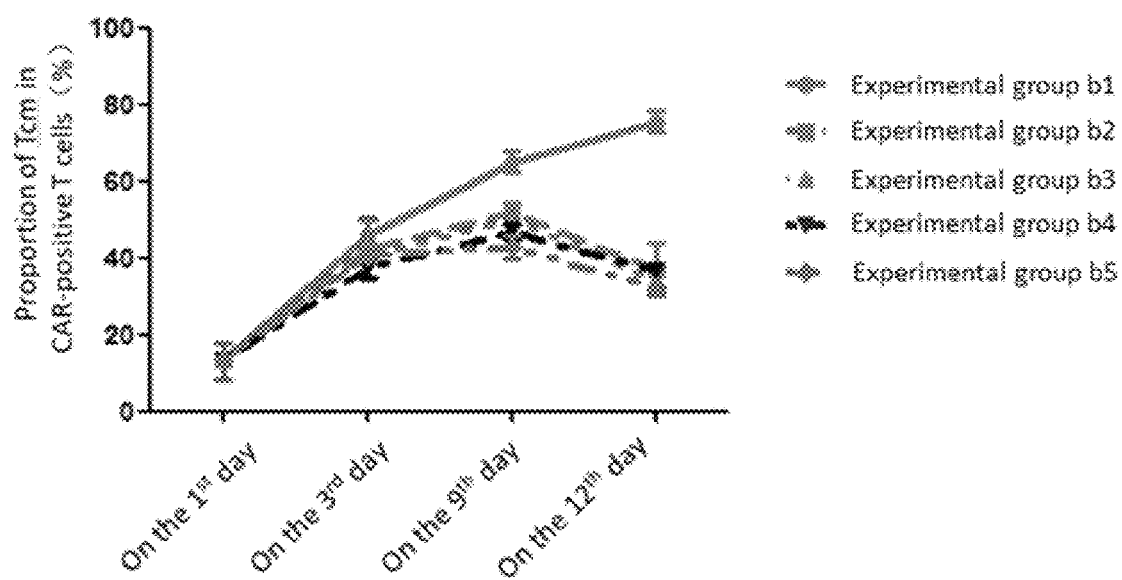
FIG. 8 illustrates changes of the proportion of the Tcm in a culture system with the increase of the culture time during the preparation of a cell product in each experimental group in embodiment 4.
Figure 9:
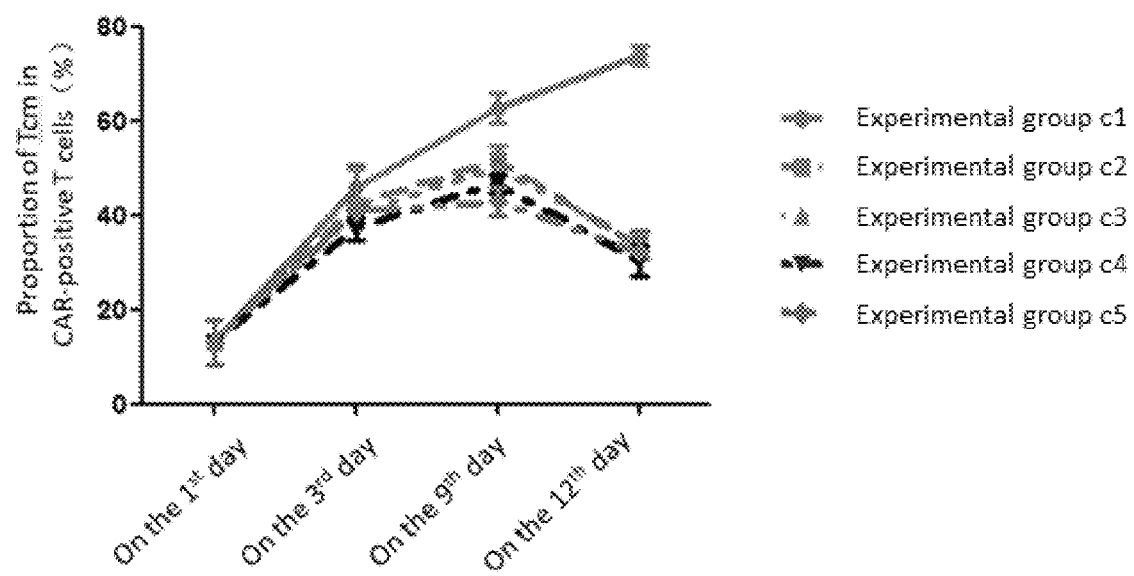
FIG. 9 illustrates changes of the proportion of the Tcm in a culture system with the increase of the culture time during the preparation of a cell product in each experimental group in embodiment 5.

The proliferation condition of a Tcm subset in the culture process was analyzed, and the analysis results are shown in FIG. 7-9. It can be learned from FIG. 7-9 that the proportion of the Tcm subset in the CAR-positive T cells in the experimental groups a1, b1, and c1 was increased significantly at the beginning of the culture, and the proliferation proportion did not change significantly as culture time was extended. The Tcm proportion in other experimental group culture systems was increased at the beginning of the culture, but the proportion was gradually decreased with the increase of the culture time. This shows that the preparation method provided in the present disclosure effectively overcomes the limitation that the Tem cannot be long-term cultured in vitro, prolongs its culture time in vitro, and guarantees the number of cells and the proportion of the Tem subset when the final product is harvested.

Embodiment 7 In Vitro Killing Activity

Figure 10:
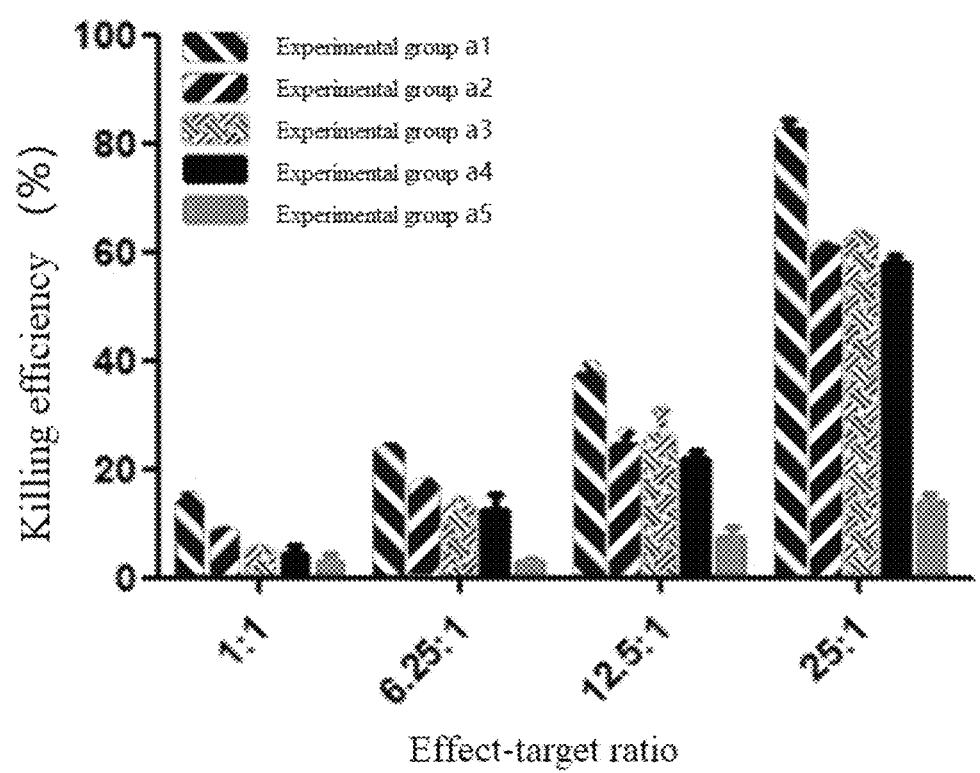
FIG. 10 illustrates an in vitro killing activity test result of a cell product prepared in each experimental group in embodiment 3.

A human lymphoma cell line Raji was used as target cells, and was inoculated into a U-bottom 96-well plate at $5\times10^4$/mL. CAR-T cells of each experimental group prepared in Embodiment 3 were co-cultured according to the effect-target ratio (E/T) ratio of 25:1, 12.5:1, 6.25:1, and 1:1. A culture medium is a serum-free RPMI1640 culture medium. The culture condition is 37° C. and 5% $CO_2$ saturated humidity incubator. After culture for 12 h, the killing activity of the CAR-T cells in different experimental groups on target cells is detected by using a lactate dehydrogenase release method (LDH method), and the detection results are shown in FIG. 10. According to experimental results in FIG. 10, under the condition of the same effect-target ratio, the killing activity of a CAR-T cell product obtained by the preparation method of the present disclosure is significantly better than that of other experimental groups, and it also indicates that the CAR-T cell product with a higher Tcm proportion has a better target cell-killing activity.

Embodiment 8 Detection of Killing-Related Cytokine Release Ability

Figure 11:
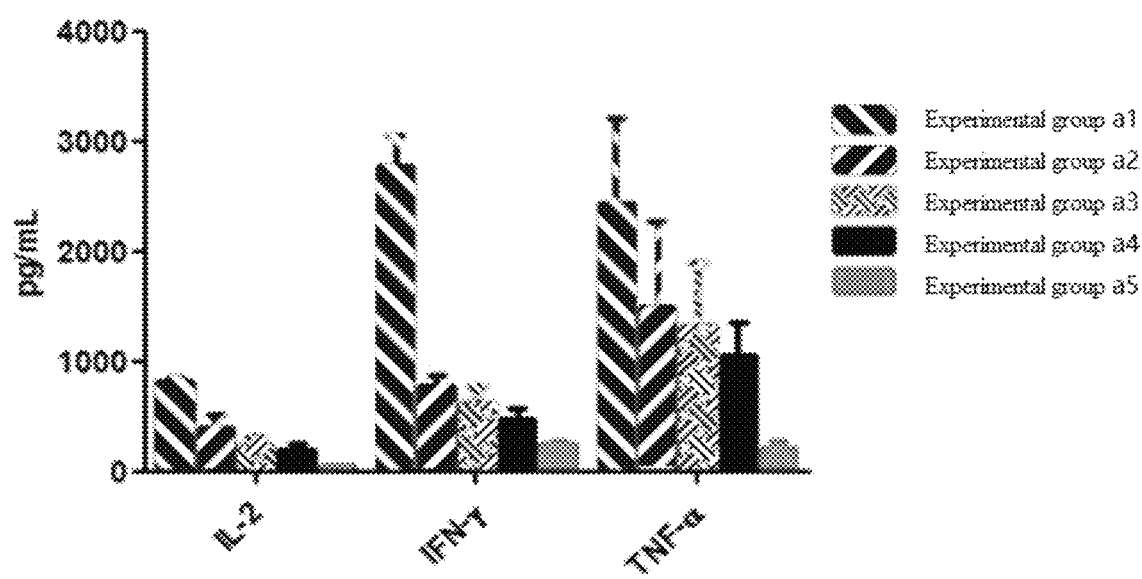
FIG. 11 illustrates an in vitro killing-related cytokine (IL-2, IFN-γ, TNF-α) release level of a cell product prepared in each experimental group in embodiment 3.

According to the method of Embodiment 7, CAR-T cells of each experimental group prepared in Embodiment 3 were mixed with Raji target cells at a ratio of 25:1, and after co-culture for 12 h, a culture supernatant was collected, and a CAR-T killing-related cytokine (IL-2, IFN-γ, TNF-α) release level is detected by using an ELISA method. As shown in the experimental results shown in FIG. 11, the CAR-T cells obtained by the preparation method of the present disclosure have a better cytokine release activity in the killing process than that of the CAR-T cells prepared by other experimental groups.

Figure 12:
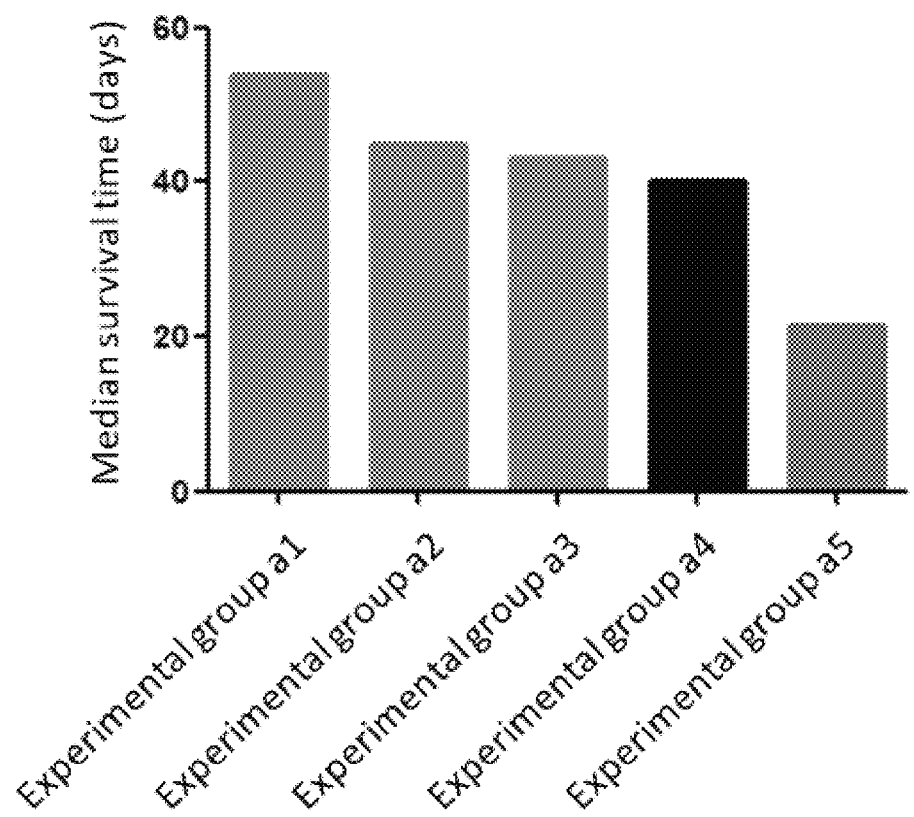
FIG. 12 illustrates an evaluation result of an in vivo anti-tumor activity of a cell product prepared in each experimental group in embodiment 3, wherein the vertical axis is a median survival time of a tumor-bearing mouse after injection of a cell product.

Embodiment 9 In-Vivo Anti-Tumor Activity Evaluation 6-8 week-old NOD/SCID IL2Rγc−/−immunodeficient mice were selected, and a tumor-bearing mouse model was established by tail intravenous injection of a human Raji cell line (Raji-Luci) stably expressing luciferase protein at a dose of $1\times10^6$/100 μL/injection. Three days after tumor cells were injected, mice were grouped according to the experiment in Embodiment 3. Each group of experimental animals was injected with CAR-T cells prepared in Embodiment 3 through caudal veins at $1\times10^6$/100 μL/injection. After the injection, a small animal imaging system was used to observe tumor progression in vivo of the experimental animals every week until all the experimental animals died. The statistical analysis results of experimental data are shown in FIG. 12. Compared with other experimental groups, the CAR-T cells obtained by the preparation method of the present disclosure can effectively prolong the median survival time of tumor-bearing mice, delay the tumor progression in vivo, and has more lasting anti-tumor activity in vivo.

Embodiment 10 Evaluation of In-Vivo Cytokine Release Activity

Figure 13:
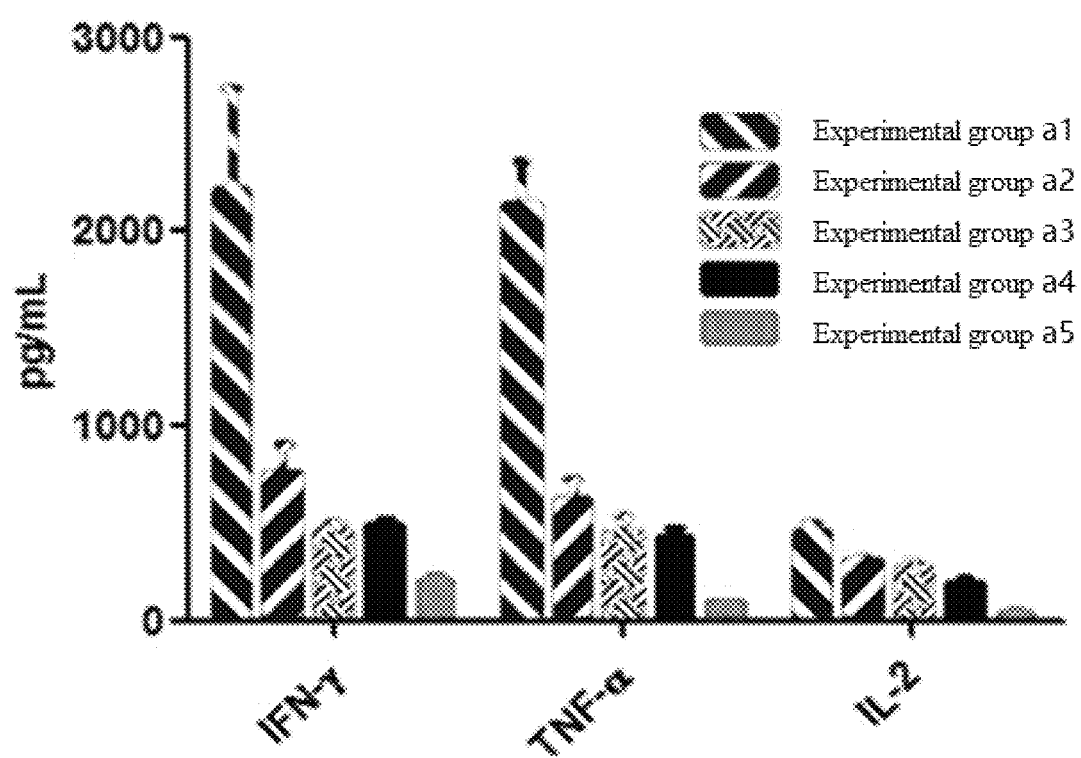
FIG. 13 illustrates an in vivo killing-related cytokine (IL-2, IFN-γ, TNF-α) release level of a cell product prepared in each experimental group in embodiment 3.
Figure 14:
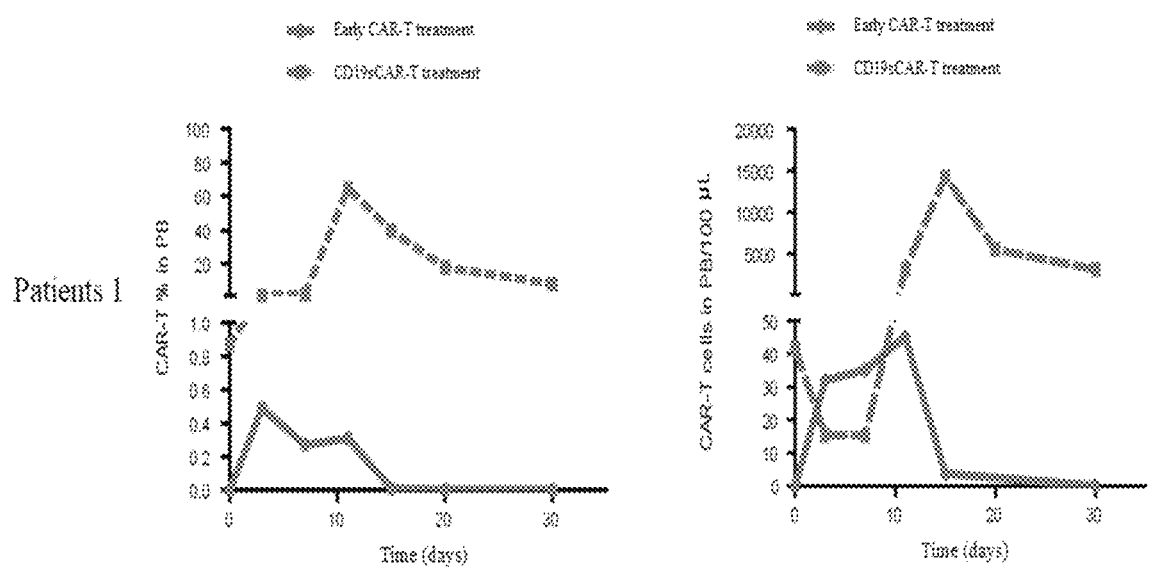
FIG. 14 illustrates detection of amplification levels of different CAR-T products in patient 1.
Figure 15:
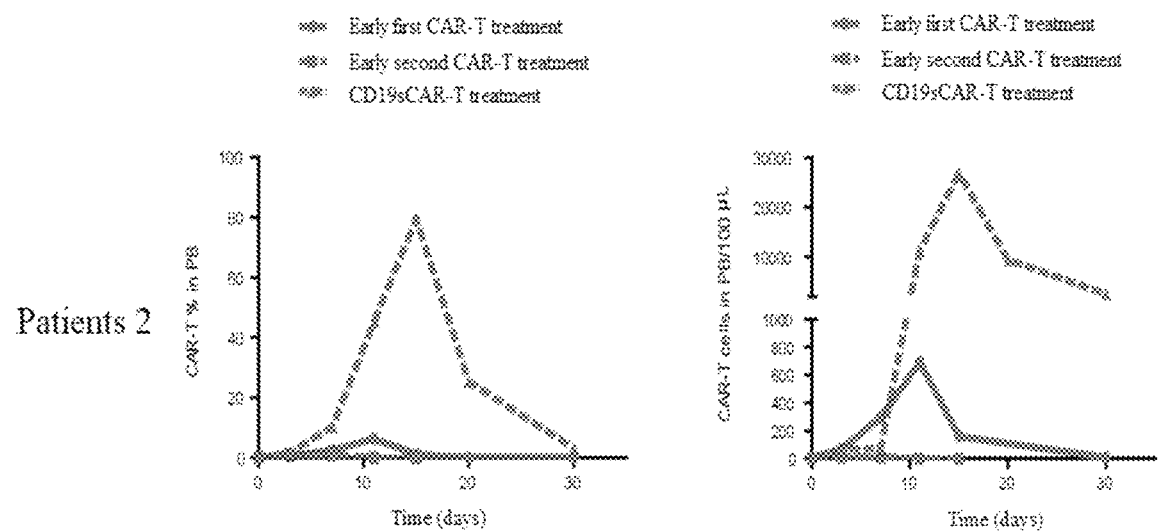
FIG. 15 illustrates detection of amplification levels of different CAR-T products in patient 2.
Figure 16:
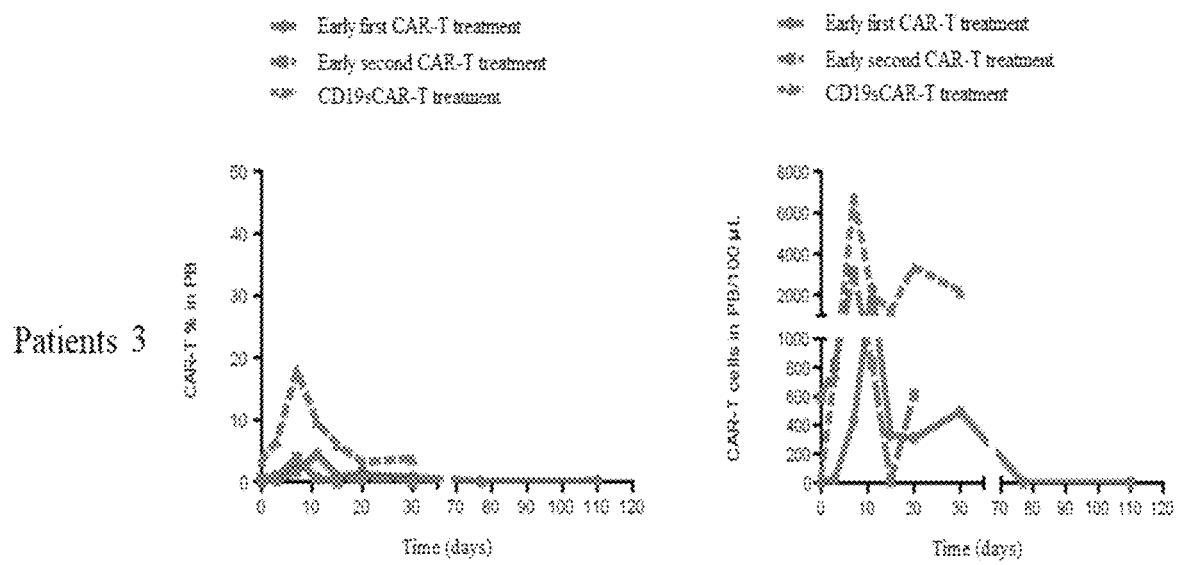
FIG. 16 illustrates detection of amplification levels of different CAR-T products in patient 3.
Figure 17:
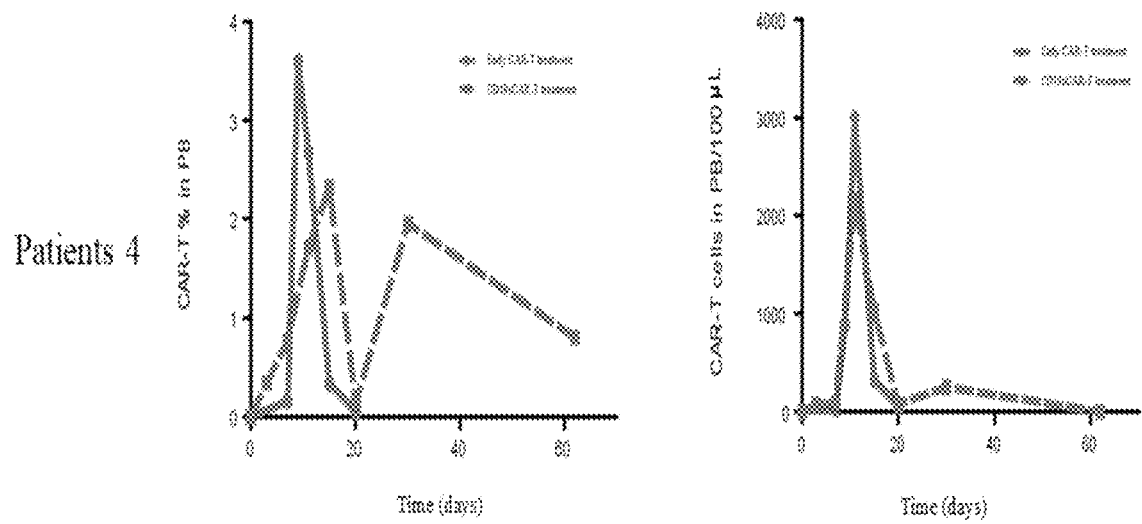
FIG. 17 illustrates detection of amplification levels of different CAR-T products in patient 4.
Figure 18:
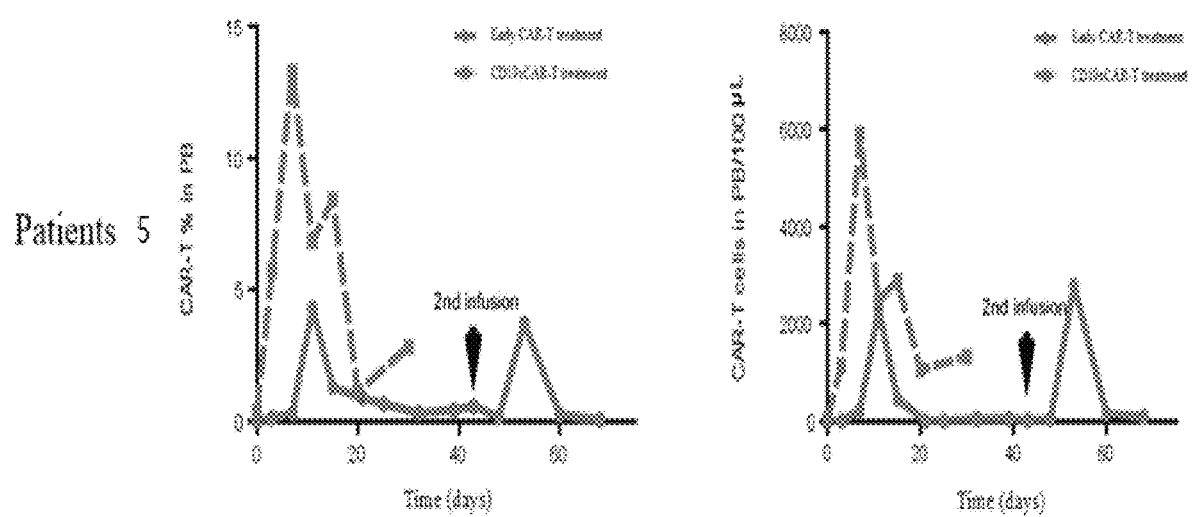
FIG. 18 illustrates detection of amplification levels of different CAR-T products in patient 5.

The levels of CAR-T-related anti-tumor cytokines (including IFN-γ, TNF-α, and IL-2) in the serums of different experimental groups of animals in Embodiment 9 are detected by using an ELISA method. The detection results are shown in FIG. 13. Compared with other experimental groups, the levels of killing-related cytokines in experimental animals receiving the CAR-T prepared by the technical solution of the present disclosure are significantly higher, indicating that they have better anti-tumor activity in vivo.

Embodiment 11 Evaluation of Clinical Safety and Effectiveness

The CD9sCAR-T cell product prepared by the experimental group a1 in Embodiment 3 was detected for clinical safety and effectiveness through a phase I clinical trial (registration number: ChiCTR1800017439, ChiCTR1800014761).

Five patients with acute B lymphocytic leukemia who have relapsed after previous treatment with mouse-derived CD19CAR-T have received a CD9sCAR-T product prepared by the experimental group a1 in Embodiment 3 of the present disclosure, and each patient received a single infusion. The infusion dose range is $0.3\times10^6$/kg-$3\times10^6$/kg. All patients receive safety evaluation weekly after the infusion and receives effectiveness evaluation on the $15^{th}$ day and the $30^{th}$ day.

A first patient was male, 9 years old, and had acute B lymphocytic leukemia. After being relapsed from standard chemotherapy treatment, he received the autologous mouse-derived CD19CAR-T and CD22CAR-T dual-targeted CAR-T treatment, and he relapsed after one month of treatment. After relapse, the patient received the autologous CD19sCAR-T treatment, the infusion dose was $1\times10^6$/kg, the bone marrow morphological tumor load level before infusion was 4%, and flow detection was 2.28%. Prior to infusion, the patient received a standard fludarabine/cyclophosphamide (F/C) scheme for lymphocyte clearance. On the $7^{th}$ day after the infusion, the patient had a fever for 3 days. After treatment, the body temperature was normal. Effectiveness evaluation was performed on the $30^{th}$ day after the infusion, and complete remission was achieved. A second patient was male, 14 years old, had the acute B lymphocytic leukemia with complex karyotypes, and had relapsed after receiving standard chemotherapy remission. Before receiving CD19sCAR-T, he was respectively treated with the mouse-derived CD19CAR-T and the mouse-derived CD19CAR-T/CD22CAR-T dual-targeted CAR-T. A first treatment achieved complete remission (CR), which lasted about three and a half months; and a second treatment was ineffective, and the tumor burden of the patient after treatment increased compared with that before the treatment (bone marrow morphology detection before the infusion: 0.5%, flow detection: 0.53%, fusion gene quantification: 0.94%; bone marrow morphology detection after 15 days of the infusion: 1.5%, the flow detection: 0.6%, the fusion gene quantification: 13.3%; bone marrow morphology detection after 36 days of the infusion: 30%, the flow detection: 46.81%, the fusion gene quantification: 119.58%.). The patient received CD19sCAR-T at a dose of $0.3 \times 10^6$/kg after the standard F/C chemotherapy, and no CRS-related side effects occurred during the treatment. The proportion of bone marrow morphological tumors evaluated on $15^{th}$ day was 10.5%, and the flow detection result was 14.98%, which was significantly lower than the corresponding index before infusion (bone marrow morphology conformance before the infusion: 46%, the flow detection: 34.86%); and however, at the $30^{th}$ day of the evaluation, the patient's bone marrow morphology conformance and flow proportion had rebounded, and are 82% and 71.84% respectively, which did not reach the CR. The third patient was male, 17 years old, had the acute B lymphocytic leukemia with central system leukemia, and had relapsed after being relieved from receiving the standard chemotherapy and mother-derived half-matched allogeneic hematopoietic stem cell transplantation therapy. After the relapse, he received two mouse-derived CD19CAR-T treatments. The complete remission was achieved after a first infusion, he relapsed on the $20^{th}$ day after a second infusion, with recurrence of the central system. After relapse, the patient received half-matched donor-derived (mother) CD19sCAR-T cell treatment, the infusion dose was $1 \times 10^6$/kg, the bone marrow morphological tumor load level before infusion was 0.5%, and the flow detection was 66.13%. Prior to the infusion, the patient received the standard fludarabine/cyclophosphamide (F/C) scheme for lymphocyte clearance. On the $5^{th}$ day after the infusion, the patient had a fever. After anti-infection treatment, the body temperature returned to normal. Effectiveness evaluation on the $30^{th}$ day after the infusion achieved complete remission. The fourth and fifth patients both were female, and respectively aged 14 and 20. Both patients had the acute B-lymphocytic leukemia, had achieved remission after the standard chemotherapy, but relapsed about 1 month after the remission. After the standard chemotherapy treatment was not effective, they received a mouse-derived CAR-T bridged half-match allogeneic hematopoietic stem cell transplantation treatment scheme. The fourth patient achieved complete remission after treatment and relapsed one and a half years later; and the fifth patient relapsed one year after treatment which achieved complete remission. In addition, before bridging transplantation, the first treatment of mouse-derived CD19CAR-T was ineffective on the fifth patient and achieved CR after the second infusion. Before CD19sCAR-T treatment, the intramedullary morphological load of the two patients was 29% and 6%, respectively, and the flow detection results were 15.31% and 34.74%, respectively. No tumor cells were found in the peripheral and cerebrospinal fluid. After receiving a standard F/C chemotherapy pretreatment, both patients received the donor-derived CD19sCAR-T treatment at a dose of $3 \times 10^6$/kg; and after the infusion, both patients developed a mild CRS reaction around the $7^{th}$ day after the infusion, and the main symptom was fever. After corresponding treatment is given, the symptom disappeared, and the two patients were evaluated for achieving CR on the $30^{th}$ day after the infusion.

The research result is shown in Table 4, four of the five patients were evaluated as patients achieving complete remission on the $30^{th}$ day, and the overall remission rate was 80%. None of the five patients had grade 3 or higher toxic and side effects.

Compared with CAR-T in vivo amplification data monitored after the patient received CD19CAR-T treatment in an early stage, the in vivo amplification level of the CD9sCAR-T prepared by the technical solution of the present disclosure is significantly higher than that of the early stage CD19CAR-T (FIG. 14-18). The research results of this embodiment show that the CD19sCAR-T prepared by the technical solution of the present disclosure has good safety and effectiveness in clinical application, and has excellent in vivo amplification capacity.

TABLE 4

Basic Information of Subjects and Evaluation of Clinical Efficacy

| NO. of Subjects | | 1 | 2 | 3 | | 4 | 5 | |
|---|---|---|---|---|---|---|---|---|
| Age | | 9 | 14 | 17 | | 14 | 20 | |
| Gender | | M | M | M | | F | F | |
| Complex chromosome situation | | N | Y | N | | N | Y | |
| Fusion gene situation | | E2A-HLF | E2A-HLF | BCR-ABL1 | | MLL/ITD | MLL/ITD | |
| Previous CAR-T treatment | CAR receptor scFv region species origin | Mouse source | Mouse source | Mouse source | | Mouse source | Mouse source | |
| | CAR identifying targets | CD19 + CD22 | CD19 | CD19 + CD22 | CD19 | CD19 | CD19 | CD19 |
| | Infusion dose ($\times 10^6$/kg) | 0.3 | 0.3 | 0.3 | 4 | 0.3 | 1 | 1 | 1 |
| | Time to recurrence after infusion (months) | 1 | 3.5 | NR | 8 | 1 | N/A* | NR | N/A* |
| Tumor load before CD19sCAR-T infusion | Bone marrow (morphology) % | 4 | 46 | 0.5 | | 29 | 6 | |
| | Bone marrow (flow) % | 2.28 | 34.86 | 0 | | 15.31 | 34.74 | |
| | Cerebrospinal fluid % | 0 | 0 | 66.13 | | 0 | 0 | |
| | Peripheral blood % | 0 | 0 | 0 | | 0 | 0 | |

TABLE 4-continued

Basic Information of Subjects and Evaluation of Clinical Efficacy

| NO. of Subjects | | | 1 | 2 | 3 | 4 | 5 |
|---|---|---|---|---|---|---|---|
| Infusion dose (×10$^6$/kg) | | | 1 | 0.3 | 1 | 3 | 3 |
| Tumor load after CD19sCAR-T treatment | Bone marrow (morphology) % | On 30$^{th}$ day | 0 | 82 | 0 | 0 | 0 |
| | Bone marrow (flow) % | | 0 | 71.84 | 0 | 0 | 0 |
| | Cerebro spinal fluid % | | 0 | 0 | 0 | 0 | 0 |
| | Peripheral blood % | | 0 | 0 | 0 | 0 | 0 |
| Cytokine storm side effects and corresponding treatment | Grade | | 1 | 1 | 1 | 1 | 1 |
| | Tocilizumab intervention or not | | N | N | N | N | N |
| | Neurotoxicity | | N | N | N | N | N |
| Evaluation results of 1 month after infusion | | | CMR, MRD- | NR | CMR, MRD- | CMR, MRD- | CMR, MRD- |

Description:
CMR: complete molecular response
F: female
M: male
MRD: minimal residual disease
N/A*: The fourth and fifth patients received half-matched allogeneic hematopoietic stem cell transplantation shortly after achieving CR with mouse-derived CD19CAR-T treatment, so the response time could not be evaluated
N: No
NR: non-remission
Y: Yes In the method for increasing the proportion of a central memory T cell (Tcm) subset in a CAR-T cell product disclosed in the present disclosure, an artificial antigenic epitope is added in a CAR, and a CAR-T is activated by the artificial antigenic epitope. The method can not only increase the proportion of CAR-positive T cells in the CAR-T cell product, but also achieve specific in vitro amplification of a Tcm subset in the CAR-positive T cells, and significantly increases the proportion of Tcm in the CAR-T cell product. Clinical trials show that the CAR-T cells prepared by the present disclosure have significantly better amplification capacity in vivo than the prior art, and have better clinical safety and effectiveness.

While this specification contains many specific implementation details, these should not be construed as limitations on the scope of any claims, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination.

Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described components and systems can generally be integrated together in a single product or packaged into multiple products.

As such, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking or parallel processing can be utilized.

It is intended that the specification and embodiments be considered as examples only. Other embodiments of the disclosure will be apparent to those skilled in the art in view of the specification and drawings of the present disclosure. That is, although specific embodiments have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the example embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

What is claimed is:

1. A method for increasing a yield of a central memory T cell (Tcm), wherein an artificial antigenic epitope is added in a CAR, and a CAR-T is activated by the artificial antigenic epitope; wherein the artificial antigenic epitope is located in an extracellular domain of the CAR, between the extracellular domain and a hinge region, or between the hinge region and a transmembrane structure, and the artificial antigenic epitope does not affect a binding between the CAR and an antigen targeted by the CAR; and the method comprising:
   (1) introducing the CAR into a T cell; and
   (2) culturing the CAR-introduced T cell, and performing specific activation in a culture process;
wherein the specific activation comprises adding an anti-artificial antigenic epitope antibody in the culture process, and the anti-artificial antigenic epitope antibody specifically recognizes the artificial antigenic epitope; in step (2), a concentration of the anti-artificial antigenic epitope antibody is 1-50 pg/mL; a method for adding the anti-artificial antigenic epitope antibody is:

encapsulating the anti-artificial antigenic epitope antibody in a culture container; in step (2), a culture medium used for culture comprises IL-7, IL-2, and IL-15, wherein a concentration of IL-7 is 10-200 ng/mL, a concentration of IL-2 is 20-1000 IU/mL, a concentration of IL-15 is 1-50 ng/mL; wherein the method does not comprise a step of specifically sorting the CAR-introduced T cells, the artificial antigenic epitope is an E-tag comprising the amino acid sequence of KPLPEVTDEY (SEQ ID NO: 1), and the anti-artificial antigenic epitope antibody is an anti-E-tag antibody comprising the amino acid sequence of SEQ ID NO: 4.

* * * * *

SEQUENCE LISTING

<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: synthesized in the laboratory

<400> SEQUENCE: 1

Lys Pro Leu Pro Glu Val Thr Asp Glu Tyr
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthesized in the laboratory

<400> SEQUENCE: 2

Trp Ser His Pro Gln Phe Glu Lys
1               5

<210> SEQ ID NO 3
<211> LENGTH: 9
<212> TYPE: PRT
<213> ORGANISM: Artificial Sequence
<220> FEATURE:
<223> OTHER INFORMATION: synthesized in the laboratory

<400> SEQUENCE: 3

Asn Trp Ser His Pro Gln Phe Glu Lys
1               5

<210> SEQ ID NO 4
<211> LENGTH: 577
<212> TYPE: PRT
<213> ORGANISM: Artificial Sequence
<220> FEATURE:
<223> OTHER INFORMATION: synthesized in the laboratory

<400> SEQUENCE: 4

Asp Ile Val Leu Thr Gln Thr Thr Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Pro Lys Asn Tyr Leu Ala Trp Tyr Gln Gln Lys Pro Gly Gln
            35                  40                  45

Ser Pro Lys Leu Leu Ile Tyr Trp Ala Ser Thr Arg Lys Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Leu Thr Phe Gly Ala Gly Thr Lys Leu Glu Leu Lys
                100                 105                 110

Gly Gly Gly Gly Ser Gly Gly Gly Ser Gly Gly Gly Ser Gln
            115                 120                 125

Val Gln Leu Glu Glu Ser Gly Ala Glu Leu Val Lys Pro Gly Ala Ser
        130                 135                 140

Val Lys Leu Ser Cys Lys Ala Ser Gly Tyr Ala Phe Thr His Tyr Tyr

-continued

```
            145                 150                 155                 160
        Ile Tyr Trp Ile Lys Gln Arg Pro Gly Gln Gly Leu Glu Trp Ile Gly
                        165                 170                 175

Gly Val Asn Pro Ser Asn Gly Gly Thr His Phe Asn Glu Lys Phe Lys
                        180                 185                 190

Ser Lys Ala Thr Leu Thr Val Asp Lys Ser Ser Ser Thr Ala Tyr Met
                        195                 200                 205

Gln Leu Ser Ser Leu Thr Ser Glu Asp Ser Ala Val Tyr Tyr Cys Thr
                210                 215                 220

Arg Ser Glu Tyr Asp Tyr Gly Leu Gly Phe Ala Tyr Trp Gly Gln Gly
        225                 230                 235                 240

Thr Leu Val Thr Val Ser Ala Ala Ser Thr Lys Gly Pro Ser Val Phe
                        245                 250                 255

Pro Leu Ala Pro Ser Ser Lys Ser Thr Ser Gly Gly Thr Ala Ala Leu
                        260                 265                 270

Gly Cys Leu Val Lys Asp Tyr Phe Pro Glu Pro Val Thr Val Ser Trp
                        275                 280                 285

Asn Ser Gly Ala Leu Thr Ser Gly Val His Thr Phe Pro Ala Val Leu
                        290                 295                 300

Gln Ser Ser Gly Leu Tyr Ser Leu Ser Ser Val Val Thr Val Pro Ser
        305                 310                 315                 320

Ser Ser Leu Gly Thr Gln Thr Tyr Ile Cys Asn Val Asn His Lys Pro
                        325                 330                 335

Ser Asn Thr Lys Val Asp Lys Lys Val Glu Pro Lys Ser Cys Asp Lys
                        340                 345                 350

Thr His Thr Cys Pro Pro Cys Pro Ala Pro Glu Leu Leu Gly Gly Pro
                        355                 360                 365

Ser Val Phe Leu Phe Pro Pro Lys Pro Lys Asp Thr Leu Met Ile Ser
                        370                 375                 380

Arg Thr Pro Glu Val Thr Cys Val Val Val Asp Val Ser His Glu Asp
        385                 390                 395                 400

Pro Glu Val Lys Phe Asn Trp Tyr Val Asp Gly Val Glu Val His Asn
                        405                 410                 415

Ala Lys Thr Lys Pro Arg Glu Glu Gln Tyr Asn Ser Thr Tyr Arg Val
                        420                 425                 430

Val Ser Val Leu Thr Val Leu His Gln Asp Trp Leu Asn Gly Lys Glu
                        435                 440                 445

Tyr Lys Cys Lys Val Ser Asn Lys Ala Leu Pro Ala Pro Ile Glu Lys
                450                 455                 460

Thr Ile Ser Lys Ala Lys Gly Gln Pro Arg Glu Pro Gln Val Tyr Thr
        465                 470                 475                 480

Leu Pro Pro Ser Arg Asp Glu Leu Thr Lys Asn Gln Val Ser Leu Thr
                        485                 490                 495

Cys Leu Val Lys Gly Phe Tyr Pro Ser Asp Ile Ala Val Glu Trp Glu
                        500                 505                 510

Ser Asn Gly Gln Pro Glu Asn Asn Tyr Lys Thr Thr Pro Pro Val Leu
                        515                 520                 525

Asp Ser Asp Gly Ser Phe Phe Leu Tyr Ser Lys Leu Thr Val Asp Lys
                        530                 535                 540

Ser Arg Trp Gln Gln Gly Asn Val Phe Ser Cys Ser Val Met His Glu
        545                 550                 555                 560

Ala Leu His Asn His Tyr Thr Gln Lys Ser Leu Ser Leu Ser Pro Gly
                        565                 570                 575
```

Lys

<210> SEQ ID NO 5
<211> LENGTH: 499
<212> TYPE: PRT
<213> ORGANISM: Artificial Sequence
<220> FEATURE:
<223> OTHER INFORMATION: synthesized in the laboratory

<400> SEQUENCE: 5

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Val Arg Pro Gly Ser Ser Val Lys Ile Ser Cys Lys Ala Ser Gly Tyr
        35                  40                  45

Ala Phe Ser Ser Tyr Trp Met Asn Trp Val Lys Gln Arg Pro Gly Gln
    50                  55                  60

Gly Leu Glu Trp Ile Gly Gln Ile Trp Pro Gly Asp Gly Asp Thr Asn
65                  70                  75                  80

Tyr Asn Gly Lys Phe Lys Gly Lys Ala Thr Leu Thr Ala Asp Glu Ser
                85                  90                  95

Ser Ser Thr Ala Tyr Met Gln Leu Ser Ser Leu Ala Ser Glu Asp Ser
            100                 105                 110

Ala Val Tyr Phe Cys Ala Arg Arg Glu Thr Thr Thr Val Gly Arg Tyr
        115                 120                 125

Tyr Tyr Ala Met Asp Tyr Trp Gly Gln Gly Thr Thr Val Thr Val Ser
    130                 135                 140

Ser Gly Gly Gly Gly Ser Lys Pro Leu Pro Glu Val Thr Asp Glu Tyr
145                 150                 155                 160

Gly Gly Gly Gly Ser Asp Ile Gln Leu Thr Gln Ser Pro Ala Ser Leu
                165                 170                 175

Ala Val Ser Leu Gly Gln Arg Ala Thr Ile Ser Cys Lys Ala Ser Gln
            180                 185                 190

Ser Val Asp Tyr Asp Gly Asp Ser Tyr Leu Asn Trp Tyr Gln Gln Ile
        195                 200                 205

Pro Gly Gln Pro Pro Lys Leu Leu Ile Tyr Asp Ala Ser Asn Leu Val
    210                 215                 220

Ser Gly Ile Pro Pro Arg Phe Ser Gly Ser Gly Ser Gly Thr Asp Phe
225                 230                 235                 240

Thr Leu Asn Ile His Pro Val Glu Lys Val Asp Ala Ala Thr Tyr His
                245                 250                 255

Cys Gln Gln Ser Thr Glu Asp Pro Trp Thr Phe Gly Gly Gly Thr Lys
            260                 265                 270

Leu Glu Ile Lys Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
            340                 345                 350
```

```
Leu Tyr Ile Phe Lys Gln Pro Phe Met Arg Pro Val Gln Thr Thr Gln
            355                 360                 365

Glu Glu Asp Gly Cys Ser Cys Arg Phe Pro Glu Glu Gly Gly
    370                 375                 380

Cys Glu Leu Arg Val Lys Phe Ser Arg Ser Ala Asp Ala Pro Ala Tyr
385                 390                 395                 400

Lys Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 6
<211> LENGTH: 1500
<212> TYPE: DNA
<213> ORGANISM: Artificial Sequence
<220> FEATURE:
<223> OTHER INFORMATION: synthesized in the laboratory

<400> SEQUENCE: 6
atggctctgc cagtgacagc tctgctgctg cctctggctc tgctgctgca cgcagctaga      60
ccccaggtgc agctgcagca gtcaggagca gaactcgtga ccaggcag cagcgtgaag      120 atctcttgca aggccagcgg ctacgccttc tctagctatt ggatgaattg ggtgaagcag      180
cggccaggac agggactgga gtggattgga cagatttggc ccggcgacgg cgataccaac      240
tacaacggca agttcaaggg caaggccacc ctgacagccg acgagtctag cagcacagcc      300
tacatgcagc tgagctctct ggccagcgag gatagcgccg tgtacttttg cgccagaagg      360
gagaccacaa cagtgggccg gtactactac gccatggact attggggcca gggcacaacc      420
gtgacagtgt ctagcggagg aggcggctct aagcctctgc agaagtgac agacgagtac      480 ggcggaggag gaagcgacat ccagctgacc cagagcccag cttctctggc agtgtctctg      540
ggacagaggg ctaccatctc ttgcaaggcc agccagagcg tggattacga cggcgacagc      600
tacctgaatt ggtatcagca gatccccggc cagcctccta agctgctgat ctacgacgcc      660
tccaacctgg tgtccggcat ccctcccaga ttcagcggaa gcggcagcgg cacagacttc      720
accctgaaca tccaccccgt ggagaaggtg acgccgcca cataccattg ccagcagagc      780
acagaggacc cctggacctt tggcggcgga acaaagctgg agatcaagac aaccacccca      840
gcccctagac ctcctacacc agcccctaca atcgcctctc agcctctgag cctgaggcca      900
gaagcttgta gacccgcagc aggaggagca gtgcatacaa ggggcctgga cttcgcttgc      960
gacatctaca tttgggcccc tctggcagga acttgcggag tgctgctgct gtctctggtc     1020
atcaccctgt attgcaagcg gggccggaag aagctgctgt acatcttcaa gcagcccttc     1080
atgcggccag tgcagacaac acaggaggag gacggttgca gctgcagatt cccagaggag     1140
gaggaaggcg gctgcgagct gagagtgaag ttcagcagga gcgccgacgc tccagcctat     1200
```

```
aaacagggac agaaccagct gtacaacgag ctgaacctgg gcagaagaga ggagtacgac   1260
gtgctggaca agaggagagg cagagaccca gagatgggcg gcaagcctag aaggaagaac   1320
ccccaggagg gcctgtacaa cgagctgcag aaggacaaga tggccgaggc ttacagcgag   1380
atcggcatga agggcgagag gagaagaggc aaaggccacg acggactgta tcagggactg   1440
agcacagcca ccaaggacac ctacgacgct ctgcacatgc aggctctgcc tcctagataa   1500
```

<210> SEQ ID NO 7
<211> LENGTH: 486
<212> TYPE: PRT
<213> ORGANISM: Artificial Sequence
<220> FEATURE:
<223> OTHER INFORMATION: synthesized in the laboratory

<400> SEQUENCE: 7

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320
```

```
Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
            370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 8
<211> LENGTH: 1461
<212> TYPE: DNA
<213> ORGANISM: Artificial Sequence
<220> FEATURE:
<223> OTHER INFORMATION: synthesized in the laboratory

<400> SEQUENCE: 8
atggctctgc cagtgacagc tctgctgctg cctctggctc tgctgctgca cgcagctaga      60
cccgacatcc agatgaccca gaccaccagc tctctgagcg cttctctggg cgacagagtg     120
accatctctt gcagggccag ccaggacatc agcaagtacc tgaattggta tcagcagaag     180
cccgacggca cagtgaagct gctgatctac cacacaagca gactgcacag cggagtgcct     240
agcagattca gcggcagcgg aagcggaacc gactacagcc tgaccatcag caacctggag     300
caggaggaca tcgccaccta cttctgccag cagggcaaca ccctgcctta cacattcggc     360
ggcggcacaa agctggagat cacaggagga ggaggaagcg gaggaggagg aagcggagga     420
ggaggaagcg aagtgaagct gcaggagagc ggaccaggac tggtggctcc ttcacagtct     480
ctgagcgtga cttgcaccgt gtcaggagtg tccctgccag actacggcgt gtcttggatc     540
aggcagcctc ctagaaaggg actggagtgg ctggagtgat ttggggaag cgagaccacc     600 tactacaaca cgcccctgaa gagccggctg accatcatca ggacaacag caagagccag     660 gtgttcctga agatgaacag cctgcagacc gacgacaccg ccatctacta ctgcgccaag     720
cactactact acggcggcag ctacgccatg gactattggg gacagggcac cagcgtgaca     780
gtgtctagca caaccacccc agcccctaga cctcctacac cagcccctac aatcgcctct     840
cagcctctga gcctgaggcc agaagcttgt agacccgcag caggaggagc agtgcataca     900
aggggcctgg acttcgcttg cgacatctac atttgggccc ctctggcagg aacttgcgga     960
gtgctgctgc tgtctctggt catcaccctg tattgcaagc ggggccggaa gaagctgctg    1020
tacatcttca gcagcccctt catgcggcca gtgcagacaa cacaggagga ggacggttgc    1080
```

-continued

```
agctgcagat tcccagagga ggaggaaggc ggctgcgagc tgagagtgaa gttcagcagg    1140
agcgccgacg ctccagccta taaacaggga cagaaccagc tgtacaacga gctgaacctg    1200
ggcagaagag aggagtacga cgtgctggac aagaggagag gcagagaccc agagatgggc    1260
ggcaagccta aaggaagaa cccccaggag ggcctgtaca cgagctgca aaggacaag      1320 atggccgagg cttacagcga gatcggcatg aagggcgaga ggagaagagg caaaggccac    1380
gacggactgt atcagggact gagcacagcc accaaggaca cctacgacgc tctgcacatg    1440
caggctctgc ctcctagata a                                              1461
```

<210> SEQ ID NO 9
<211> LENGTH: 497
<212> TYPE: PRT
<213> ORGANISM: Artificial Sequence
<220> FEATURE:
<223> OTHER INFORMATION: synthesized in the laboratory

<400> SEQUENCE: 9

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Val Arg Pro Gly Ser Ser Val Lys Ile Ser Cys Lys Ala Ser Gly Tyr
        35                  40                  45

Ala Phe Ser Ser Tyr Trp Met Asn Trp Val Lys Gln Arg Pro Gly Gln
    50                  55                  60

Gly Leu Glu Trp Ile Gly Gln Ile Trp Pro Gly Asp Gly Asp Thr Asn
65                  70                  75                  80

Tyr Asn Gly Lys Phe Lys Gly Lys Ala Thr Leu Thr Ala Asp Glu Ser
                85                  90                  95

Ser Ser Thr Ala Tyr Met Gln Leu Ser Ser Leu Ala Ser Glu Asp Ser
            100                 105                 110

Ala Val Tyr Phe Cys Ala Arg Arg Glu Thr Thr Thr Val Gly Arg Tyr
        115                 120                 125

Tyr Tyr Ala Met Asp Tyr Trp Gly Gln Gly Thr Thr Val Thr Val Ser
    130                 135                 140

Ser Gly Gly Gly Gly Ser Trp Ser His Pro Gln Phe Glu Lys Gly Gly
145                 150                 155                 160

Gly Gly Ser Asp Ile Gln Leu Thr Gln Ser Pro Ala Ser Leu Ala Val
                165                 170                 175

Ser Leu Gly Gln Arg Ala Thr Ile Ser Cys Lys Ala Ser Gln Ser Val
            180                 185                 190

Asp Tyr Asp Gly Asp Ser Tyr Leu Asn Trp Tyr Gln Gln Ile Pro Gly
        195                 200                 205

Gln Pro Pro Lys Leu Leu Ile Tyr Asp Ala Ser Asn Leu Val Ser Gly
    210                 215                 220

Ile Pro Pro Arg Phe Ser Gly Ser Gly Ser Gly Thr Asp Phe Thr Leu
225                 230                 235                 240

Asn Ile His Pro Val Glu Lys Val Asp Ala Ala Thr Tyr His Cys Gln
                245                 250                 255

Gln Ser Thr Glu Asp Pro Trp Thr Phe Gly Gly Gly Thr Lys Leu Glu
            260                 265                 270

Ile Lys Thr Thr Thr Pro Ala Pro Arg Pro Thr Pro Ala Pro Thr
        275                 280                 285
```

-continued

```
Ile Ala Ser Gln Pro Leu Ser Leu Arg Pro Glu Ala Cys Arg Pro Ala
        290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Gly Gly Cys Glu
370                 375                 380

Leu Arg Val Lys Phe Ser Arg Ser Ala Asp Ala Pro Ala Tyr Lys Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 10
<211> LENGTH: 1494
<212> TYPE: DNA
<213> ORGANISM: Artificial Sequence
<220> FEATURE:
<223> OTHER INFORMATION: synthesized in the laboratory

<400> SEQUENCE: 10

```
atggcgctgc cggtgaccgc gctgctgctg ccgctggcgc tgctgctgca tgcggcgcgt    60
ccgcaggtgc agctgcagca gagcggcgcg gaactggtgc gtccgggcag cagcgtgaaa   120
attagctgca aagcgagcgg ctatgcgttt agcagctatt ggatgaactg ggtgaaacag   180
cgtccgggcc agggcctgga atggattggc cagatttggc cgggcgatgg cgataccaac   240
tataacggca aatttaaagg caaagcgacc ctgaccgcgg atgaaagcag cagcaccgcg   300
tatatgcagc tgagcagcct ggcgagcgaa gatagcgcgg tgtattttg cgcgcgtcgt   360
gaaaccacca ccgtgggccg ttattattat gcgatggatt attggggcca gggcaccacc   420
gtgaccgtga gcagcggcgg cggcggcagc tggagccatc gcagtttga aaaaggcggc   480
ggcggcagcg atattcagct gacccagagc ccggcgagcc tggcggtgag cctgggccag   540
cgtgcgacca ttagctgcaa agcgagccag agcgtggatt atgatggcga tagctatctg   600
aactggtatc agcagattcc gggccagccg ccgaaactgc tgatttatga tgcgagcaac   660
ctggtgagcg gcattccgcc gcgttttagc ggcagcggca gcggcaccga ttttaccctg   720
aacattcatc cggtggaaaa agtggatgcg gcgacctatc attgccagca gagcaccgaa   780
gatccgtgga cctttggcgg cggcaccaaa ctggaaatta aaaccaccac cccggcgccg   840
```

-continued

```
cgtccgccga ccccggcgcc gaccattgcg agccagccgc tgagcctgcg tccggaagcg      900
tgccgtccgg cggcgggcgg cgcggtgcat acccgtggcc tggattttgc gtgcgatatt      960
tatatttggg cgccgctggc gggcacctgc ggcgtgctgc tgctgagcct ggtgattacc     1020
ctgtattgca aacgtggccg taaaaaactg ctgtatattt ttaaacagcc gtttatgcgt     1080
ccggtgcaga ccacccagga agaagatggc tgcagctgcc gttttccgga agaagaagaa     1140
ggcggctgcg aactgcgtgt gaaatttagc cgtagcgcgg atgcgccggc gtataaacag     1200
ggccagaacc agctgtataa cgaactgaac ctgggccgtc gtgaagaata tgatgtgctg     1260
gataaacgtc gtggccgtga tccggaaatg ggcggcaaac cgcgtcgtaa aaacccgcag     1320
gaaggcctgt ataacgaact gcagaaagat aaaatggcgg aagcgtatag cgaaattggc     1380
atgaaaggcg aacgtcgtcg tggcaaaggc catgatggcc tgtatcaggg cctgagcacc     1440
gcgaccaaag atacctatga tgcgctgcat atgcaggcgc tgccgccgcg ttaa           1494
```

<210> SEQ ID NO 11
<211> LENGTH: 498
<212> TYPE: PRT
<213> ORGANISM: Artificial Sequence
<220> FEATURE:
<223> OTHER INFORMATION: synthesized in the laboratory

<400> SEQUENCE: 11

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Val Arg Pro Gly Ser Ser Val Lys Ile Ser Cys Lys Ala Ser Gly Tyr
        35                  40                  45

Ala Phe Ser Ser Tyr Trp Met Asn Trp Val Lys Gln Arg Pro Gly Gln
    50                  55                  60

Gly Leu Glu Trp Ile Gly Gln Ile Trp Pro Gly Asp Gly Asp Thr Asn
65                  70                  75                  80

Tyr Asn Gly Lys Phe Lys Gly Lys Ala Thr Leu Thr Ala Asp Glu Ser
                85                  90                  95

Ser Ser Thr Ala Tyr Met Gln Leu Ser Ser Leu Ala Ser Glu Asp Ser
            100                 105                 110

Ala Val Tyr Phe Cys Ala Arg Arg Glu Thr Thr Thr Val Gly Arg Tyr
        115                 120                 125

Tyr Tyr Ala Met Asp Tyr Trp Gly Gln Gly Thr Thr Val Thr Val Ser
    130                 135                 140

Ser Gly Gly Gly Gly Ser Asn Trp Ser His Pro Gln Phe Glu Lys Gly
145                 150                 155                 160

Gly Gly Gly Ser Asp Ile Gln Leu Thr Gln Ser Pro Ala Ser Leu Ala
                165                 170                 175

Val Ser Leu Gly Gln Arg Ala Thr Ile Ser Cys Lys Ala Ser Gln Ser
            180                 185                 190

Val Asp Tyr Asp Gly Asp Ser Tyr Leu Asn Trp Tyr Gln Gln Ile Pro
        195                 200                 205

Gly Gln Pro Pro Lys Leu Leu Ile Tyr Asp Ala Ser Asn Leu Val Ser
    210                 215                 220

Gly Ile Pro Pro Arg Phe Ser Gly Ser Gly Ser Gly Thr Asp Phe Thr
225                 230                 235                 240

Leu Asn Ile His Pro Val Glu Lys Val Asp Ala Ala Thr Tyr His Cys
                245                 250                 255
```

Gln Gln Ser Thr Glu Asp Pro Trp Thr Phe Gly Gly Gly Thr Lys Leu
            260                 265                 270

Glu Ile Lys Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
370                 375                 380

Glu Leu Arg Val Lys Phe Ser Arg Ser Ala Asp Ala Pro Ala Tyr Lys
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
        450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 12
<211> LENGTH: 1497
<212> TYPE: DNA
<213> ORGANISM: Artificial Sequence
<220> FEATURE:
<223> OTHER INFORMATION: synthesized in the laboratory

<400> SEQUENCE: 12
atggcgctgc cggtgaccgc gctgctgctg ccgctggcgc tgctgctgca tgcggcgcgt     60
ccgcaggtgc agctgcagca gagcggcgcg gaactggtgc gtccgggcag cagcgtgaaa    120
attagctgca aagcgagcgg ctatgcgttt agcagctatt ggatgaactg ggtgaaacag    180
cgtccgggcc agggcctgga atggattggc cagatttggc cgggcgatgg cgataccaac    240
tataacggca aatttaaagg caaagcgacc ctgaccgcgg atgaaagcag cagcaccgcg    300
tatatgcagc tgagcagcct ggcgagcgaa gatagcgcgg tgtattttg cgcgcgtcgt    360 gaaaccacca ccgtgggccg ttattattat gcgatggatt attggggcca gggcaccacc    420
gtgaccgtga gcagcggcgg cggcggcagc aattggagcc atccgcagtt tgaaaaaggc    480
ggcggcggca gcgatattca gctgacccag agcccggcga gcctggcggt gagcctgggc    540
cagcgtgcga ccattagctg caaagcgagc cagagcgtgg attatgatgg cgatagctat    600
ctgaactggt atcagcagat tccgggccag ccgccgaaac tgctgattta tgatgcgagc    660

-continued

```
aacctggtga gcggcattcc gccgcgtttt agcggcagcg gcagcggcac cgattttacc      720
ctgaacattc atccggtgga aaaagtggat gcggcgacct atcattgcca gcagagcacc      780
gaagatccgt ggacctttgg cggcggcacc aaactggaaa ttaaaaccac cacccggcg       840 ccgcgtccgc cgaccccggc gccgaccatt gcgagccagc cgctgagcct gcgtccggaa      900
gcgtgccgtc cggcggcggg cggcgcggtg catacccgtg gcctggattt tgcgtgcgat      960
atttatattt gggcgccgct ggcgggcacc tgcggcgtgc tgctgctgag cctggtgatt     1020
accctgtatt gcaaacgtgg ccgtaaaaaa ctgctgtata tttttaaaca gccgtttatg     1080
cgtccggtgc agaccaccca ggaagaagat ggctgcagct gccgtttcc ggaagaagaa      1140 gaaggcggct gcgaactgcg tgtgaaattt agccgtagcg cggatgcgcc ggcgtataaa     1200
cagggccaga accagctgta taacgaactg aacctgggcc gtcgtgaaga atatgatgtg     1260
ctggataaac gtcgtggccg tgatccggaa atgggcggca aaccgcgtcg taaaaacccg     1320
caggaaggcc tgtataacga actgcagaaa gataaaatgg cggaagcgta tagcgaaatt     1380
ggcatgaaag gcgaacgtcg tcgtggcaaa ggccatgatg gcctgtatca gggcctgagc     1440
accgcgacca agataccta tgatgcgctg catatgcagg cgctgccgcc gcgttaa        1497
```